United States Patent [19]
Camaggi et al.

[11] Patent Number: 5,856,311
[45] Date of Patent: *Jan. 5, 1999

[54] DERIVATIVES OF β-AMINOPROPIONIC ACID WITH A FUNGICIDAL ACTIVITY

[75] Inventors: Giovanni Camaggi, Novara; Lucio Filippini, S. Donato Milanese; Marilena Gusmeroli, Monza; Silvia Mormile, Turin; Ernesto Signorini, Malnate; Carlo Garavaglia, Cuggiono, all of Italy

[73] Assignee: Isagro Ricerca Srl, Milan, Italy

[*] Notice: This patent issued on a continued prosecution application filed under 37 CFR 1.53(d), and is subject to the twenty year patent term provisions of 35 U.S.C. 154(a)(2).

[21] Appl. No.: 553,782

[22] Filed: Oct. 23, 1995

[30] Foreign Application Priority Data

Oct. 21, 1994 [IT] Italy ................ MI94A2156

[51] Int. Cl.⁶ .................... A01N 37/44
[52] U.S. Cl. ............ 514/19; 514/210; 514/365; 514/472; 514/521; 514/522; 514/531; 514/533; 514/535; 514/538; 560/21; 560/38; 560/40; 560/41
[58] Field of Search ............... 560/21, 38, 40, 560/41; 514/19, 210, 365, 472, 521, 522, 531, 533, 535, 538

[56] References Cited

PUBLICATIONS

Keirs J. Chem. Soc. Perkin Trans. 1991 1041, 1991.
Mladenva Synthetic Comm. 23(6) 725, 1993.
Palomo J. Org. Chem. 56 (6) 2244, 1991.

Journal of Labelled Compounds and Radiopharmaceuticals, vol. 31, No. 4, 1992, pp. 305–315, Wheeler, W.J. & O'Bannon, D., "A Chiral Synthesis of Dapoxetine Hydrochloride, a Serotonin Re–uptake Inhibitor, and its 14C Isotopomer."

Bulletin de la Societe Chimique de France (Part II), No. 7–8, Jul. 1983, – Aug. 1983, pp. 195–201, Yebdri, O. & Texier, F., "Addition d'azlactones ylures d'azomethine potentiels a quelaues alcenes electrophiles, en milieu anhydride acetique: obtention de pyrrolines–2 et de pyrroles N–acetyles."***.

Tetrahedron Letters, vol. 30, No. 34, 1989, pp. 4539–4542, Kaseda, T., et al., "Enantioselective total synthesis of (+)–(S)–dihydroperiphylline."

Synthesis, No. 1–2, Jan., 1992 – Feb., 1992, pp. 229–234, Denmark, S.E., "A diastereoselective synthesis of (dl)–1, 3–diphenyl–1,3–propanediamines."

CAS, STN–Registry, RN 91350–02–6 and 93013–39–9.

*Primary Examiner*—Robert Gerstl
*Attorney, Agent, or Firm*—Oblon, Spivak, McClelland, Maier & Neustadt, P.C.

[57] ABSTRACT

Compounds based on derivatives of β-aminopropionic acid having the general formula (I):

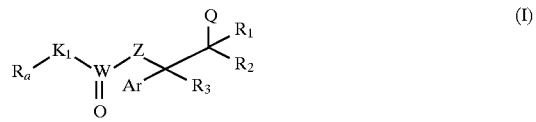

The compounds having general formula (I) have a high antifungal activity.

18 Claims, No Drawings

DERIVATIVES OF β-AMINOPROPIONIC ACID WITH A FUNGICIDAL ACTIVITY

The present invention relates to compounds based on derivatives of β-aminopropionic acid.

More specifically, the present invention relates to compounds based on derivatives of β-aminopropionic acid having a high antifungal activity, a process for their preparation and their use in the agricultural field as fungicides.

The present invention therefore relates to com- pounds based on derivatives of β-aminopropionic acid having general formula (I):

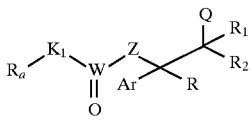

wherein:

W represents a carbon atom; a $—S(O)_m$ group wherein m is an integer between 0 and 2; or a group having general formula (II):

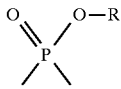

wherein:

R represents a $C_1-C_8$ alkyl or haloalkyl group, linear or branched, said alkyl or haloalkyl group also optionally substituted;

Ar represents a phenyl group; a naphthyl group; a penta or hexatomic aromatic heterocyclic group containing from 1 to 4 heteroatoms selected from nitrogen, sulphur and oxygen, said aromatic heterocyclic group possibly being benzo-condensed; or a $C_3-C_{10}$ cycloalkyl group; said phenyl, naphthyl, heterocyclic and cycloalkyl groups also being optionally substituted;

Q represents a cyano group; a thiazolic group, said thiazolic group also optionally substituted; a group having the general formula (III):

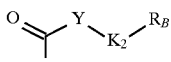

wherein

Y represents an oxygen atom; a group having the general formula (IV):

or an AA aminoacidic residue;

Z represents a group having general formula (V):

or an AA aminoacidic residue;

$R_a$ and $R_b$, the same or different, represent a hydrogen atom; a $C_1-C_8$ alkyl or haloalkyl group, linear or branched; a $C_4-C_{10}$ cycloalkylalkylic group; a phenyl group; a naphthyl group; a tetra-, pent- or hexatomic heterocyclic group containing from 1 to 4 heteroatoms selected from nitrogen, sulphur and oxygen, said aromatic heterocyclic group being possibly benzo-condensed; or a $C_3-C_{10}$ cycloalkyl group; said alkyl or haloalkyl, cycloalkylalkylic, phenyl, naphthyl, heterocyclic and cycloalkyl groups also being optionally substituted;

$K_1$ and $K_2$, the same or different, represent a direct bond; or a $C_1-C_8$ alkylenic or haloalkylenic chain, linear or branched, said alkylenic or haloalkylenic chain also optionally substituted;

$K_1$ may also represent an oxygen atom; or a $C_2-C_8$ oxa-alkylenic chain, linear or branched; or an $—NR_2—$ group, wherein $R_z$ may have the same meaning as $R_a$;

$K_2$ may also represent a $C_2-C_8$ ω-oxa-alkylenic chain, linear or branched;

$R_1$, $R_2$, $R_3$, $R_4$ and $R_5$, the same or different, represent a hydrogen atom; or a $C_1-C_8$ alkyl or haloalkyl group, linear or branched, said alkyl or haloalkyl group also being optionally substituted;

$R_1$ and $R_2$, the same or different, may also represent a fluorine atom;

$R_2$ may also represent a $C_1-C_2$ alkylenic chain which is joined to a carbon atom forming the above Ar group; or, when $K_2$ does not represent a direct bond, $R_2$ together with $R_b$, may represent a direct bond; or $R_2$ together with $R_5$, may represent a $C_1-C_8$ alkylenic or haloalkylenic chain, linear or branched; or, $R_2$ together with $R_3$, may represent a $C_1-C_8$ alkylenic or haloalkylenic chain, linear or branched; or, $R_2$ together with $R_1$, may represent a $C_1-C_8$ alkylenic or haloalkylenic chain, linear or branched; said alkylenic or haloalkylenic chain also being optionally substituted;

$R_3$ may also represent a group having general formula (III) described above;

$R_4$ together with $R_b$, when $K_2$ does not represent a direct bond, may represent a $C_1-C_2$ alkylenic chain;

$R_5$, when $R_2$ is not a $C_1-C_2$ alkylenic chain, may also represent a $C_1-C_2$ alkylenic chain which is linked to a carbon atom forming the Ar group described above;

AA represents an aminoacidic residue having general formula (VI):

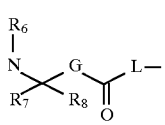

wherein:

L represents a group having general formula (VII):

G represents a direct bond; or a group having general formula (VIII):

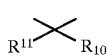

$R_6$, $R_7$, $R_8$, $R_9$, $R_{10}$ and $R_{11}$, the same or different, represent a hydrogen atom; a $C_1-C_8$ alkyl or haloalkyl group, linear or branched; a $C3-C_{10}$ cycloalkyl group; a $C_4$–$C_{10}$ cycloalkylalkylic group; or a phenyl group; said alkyl or haloalkyl, cycloalkyl, cycloalkylalkylic and phenyl groups also being optionally substituted;

$R_6$ and $R_7$, or $R_7$ and $R_{11}$ may also represent, jointly, a $C_1$–$C_8$ alkylenic, thia-alkylenic, oxa-alkylenic or haloalkylenic chain, linear or branched, said alkylenic, or thia-alkylenic, oxa-alkylenic or haloalkylenic chain also being optionally substituted;

$R_9$, when $R_2$ does not represent a $C_1$–$C_2$ alkylenic chain, may also represent a $C_1$–$C_2$ alkylenic chain which is joined to a carbon atom forming the Ar group described above; or, $R_9$ together with $R_2$, may represent a $C_1$–$C_8$ alkylenic or haloalkylenic chain, linear or branched.

The present invention also relates to the use as a fungicide of the compound having general formula (IX):

wherein $R_1$, $R_2$, $R_3$, Ar and Q, have the same meaning described above and RC may have the same meaning as $R_5$ and $R_9$.

A further object of the present invention is the use as a fungicide of the β-lactamic compound having general formula (IXa):

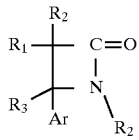

wherein $R_1$, $R_2$, $R_3$ and Ar have the same meaning described above and $R_L$ may have the same meaning as $R_c$ or can be a group having general formula (IXb):

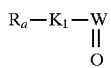

wherein $R_a$, W and $K_1$ have the same meaning described above.

The compound having general formula (IX) is an intermediate for the preparation of the compounds having general formula (I).

The compound having general formula (IXa) is the synthetic precursor for the preparation of the compound having general formula (IX).

The compounds having general formula (I) can have more than one asymmetrical centre. Comprised within the scope of the present invention are both compounds having general formula (I) isomerically pure alone, and mixtures of these in any proportion.

When a phenyl group, a naphthyl group, a thiazolic group, a penta- or hexatomic aromatic heterocyclic group or tetra-, penta- or hexatomic heterocyclic group, containing from 1 to 4 heteroatoms selected from nitrogen, sulphur and oxygen, said penta- or hexatomic aromatic heterocyclic or tetra-, penta- or hexatomic heterocyclic group being possibly benzo-condensed, a $C_3$–$C_{10}$ cycloalkyl group, a $C_4$–$C_{10}$ cycloalkylalkylic group, a $C_1$–$C_8$ alkyl or haloalkyl group, a $C_1$–$C_8$ alkylenic or haloalkylenic chain, are described as being optionally substituted, this means that said group or said chain can be substituted with one or more halogens, the same or different, selected from fluorine, chlorine, bromine and iodine, and/or with one or more groups, the same or different, selected from nitrile groups, $C_1$–$C_8$ alkyl or haloalkyl groups, linear or branched, $C_1$–$C_8$ alkoxylic or haloalkoxylic groups, linear or branched, $C_3$–$C_{10}$ cycloalkyl groups, $C_3$–$C_{10}$ cycloalkoxylic groups, $C_4$–$C_{10}$ cycloalkylalkylic groups, $C_4$–$C_{10}$ cycloalkylalkoxylic groups, $C_4$–$C_{10}$ trialkylsilylalkylic groups, $C_4$–$C_{10}$ trialkylsilylic groups, $C_4$–$C_{10}$ trialkylsilyloxylic groups, $C_4$–$C_{10}$ trialkylsilylalkoxylic groups, $C_1$–$C_9$ carboalkoxylic groups, linear or branched, $C_2$–$C_8$ alkenylic or haloalkenylic groups, linear or branched, $C_1$–$C_5$ alkoxycarbonylaminic groups, $C_1$–$C_5$ alkanoylaminic groups, phenyl or phenoxylic groups in turn optionally substituted with one or more halogens, the same or different, selected from fluorine, chlorine, bromine and iodine, or with $C_1$–$C_8$ alkyl or haloalkyl groups, linear or branched, or with $C_1$–$C_8$ alkoxylic or haloalkoxylic groups, linear or branched.

In the compounds having general formula (I) the optionally substituted phenyl group can also be substituted with a group having general formula (X):

wherein:

$R_{12}$ and $R_{13}$, the same or different, represent a hydrogen atom; a fluorine atom; or a $C_1$–$C_8$ alkyl or haloalkyl group, linear or branched.

Examples of $C_1$–$C_8$ alkyl or haloalkyl groups are: methyl, ethyl,- propyl, 2-propyl, butyl, 2-butyl, pentyl, 2-pentyl, 3-pentyl , trifluoromethyl, 1,1,2,2-tetrafluoroethyl, etc.

$C_3$–$C_{10}$ cycloalkyl groups refer to n-atomic cycloalkyls such as, for example, cyclopropane, cyclopentane, cyclooctane, etc; or cycloalkyls substituted with alkyl groups so that the total number of carbon atoms is ≤10 such as, for example, 1-methylcyclopropane, 2,2-dimethylcyclopropane, 1-methylcyclopentane, 2-methylcyclopentane, 4-ethylcyclohexane, etc.

$C_4$–$C_{10}$ cycloalkylalkylic groups refer to alkyl grous substituted with cycloalkyls so that the total number of carbon atoms is ≤10, such as, for example, cyclopropylmethyl, 1-(cyclopropyl)ethyl, 2-(cyclopropyl) propyl, 1-(2,2-dimethylcyclopropyl)ethyl, etc.

Examples of $C_1$–$C_8$ alkoxylic or haloalkoxylic groups are: methoxyl, ethoxyl, trifluoromethoxyl, 1,1,2,2-tetrafluoroethoxyl, 2,2,2-trifluoroethyoxyl, etc.

$C_3$–$C_{10}$ cycloalkoxylic groups are oxygen atoms substituted with n-atomic cycloalkyl groups such as, for example, cyclopropyloxyl, cyclopentyloxyl, cyclohexyloxyl, etc.; or $C_3$–$C_{10}$ cycloalkoxylic groups substituted with alkyls so that the total number of carbon atoms is ≤10 such as, for example, 1-methylcycloprop-1-yloxyl, 2,2-dimethylcycloprop-1-yloxyl, etc.

$C_4$–$C_{10}$ cycloalkylalkoxylic groups are alkoxylic groups substituted with cycloalkyls so that the total number of carbon atoms is ≤10 such as, for example, cyclopropylmethoxyl, 1-(cyclopropyl)ethoxyl, 1-(2-methylcyclopropyl)ethoxyl, cyclopentylmethoxyl, (4,4-dimethylcyclohexyl)methoxyl, etc.

Examples of $C_4$–$C_{10}$ trialkylsilylalkyl groups are: trimethylsilylmethyl, trimethylsilylethyl, etc.

Examples of $C_4$–$C_{10}$ trialkylsilylic groups are: trimethylsilyl, triethylsilyl, etc.

Examples of $C_4$–$C_{10}$ trialkylsilyloxylic groups are: trimethylsilyloxyl, tert-butyldimethylsilyloxyl, etc.

Examples of $C_4$–$C_{10}$ trialkylsilylalkoxylic groups are: trimethylsilylmethoxyl, etc.

$C_1$–$C_9$ carboalkoxylic groups are groups wherein $C_1$ can be identified with a carboxyl whereas $C_{n>1}$ is a carboxyl esterified with a $C_1$–$C_8$ alkoxylic group defined above.

Examples of $C_2$–$C_8$ alkenylic or haloalkenylic groups are: ethylene, propylene, butene, 2,2-dichloropropene, 1,2,2-trichloropropene, etc.

Examples of phenoxylic groups optionally substituted with one or more halogens or with $C_1$–$C_8$ alkyl or haloalkyl groups, or with $C_1$–$C_8$ alkoxylic or haloalkoxylic groups are: 4-chlorophenol, 2,4-dichlorophenol, 2-methylphenol, 4-methylphenol, 4-trifluoromethylphenol, 3-trifluoromethoxyphenol, etc.

Examples of $C_1$–$C_5$ alkoxycarbonylaminic groups are: isopropyloxycarbonylamine, tert. -butyloxycarbonylamine, etc.

Examples of $C_1$–$C_5$ alkanoylaminic groups are: acetamide, pivaloylamine, etc.

Examples of $C_1$–$C_8$ alkylenic or haloalkylenic chains are: methylene, ethylene, 1-methylethylene, 2-methylethylene, 1,1-dimethylethylene, propylene, 2,2-dime- thylpropylene, 2,2-dichloroethylene, 2,2-difluorethylene, etc.

Examples of $C_2$–$C_8$ oxa-alkylenic or ω-oxa-alkylenic chains are: 1-oxaethylene, 2-oxaethylene, 2-oxa-2-methylethylene, 2-oxapropylene, 3-oxapropylene, etc.

The AA aminoacidic residues can be selected from derivatives of natural aminoacids such as, for example, L-valine (-L[Val]N($R_9$)H-), D-valine (-D[Val]N($R_9$)H-), DL-valine (-DL[Val]N($R_9$)H-), L-leucine (-L[Leu]N($R_9$)H-), L-isoleucine (-L[Ile]N($R_9$)H-), DL-proline (-DL[Pro]N($R_9$)H-); or from derivatives of non-natural aminoacids such as, for example, DL-3-methylproline (-DL[Pro] (3-Me)N($R_9$) H-) , DL-3,3-dimethylproline(-DL[Pro] (3-Me$_2$)N($R_9$)H-), L-N-methylvaline (-L(Me) [Val]N($R_9$)H-), L-α-cyclopentylglycinamide, L-α-cyclobutylglycinamide, L-α-cyclopropylglycinamide. In the aminoacids listed, $R_9$ has the same meaning described above.

The compounds having general formula (I) can be obtained with different processes.

When Z represents a group having general formula (V), the compounds having general formula (Ia) are obtained by a process which can be schematized as follows:

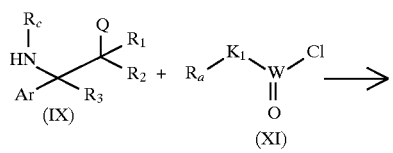 (i)

-continued

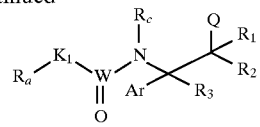

wherein $R_1$, $R_2$, $R_3$, $R_c$, $R_a$, $K_1$, Ar, Q and W have the same meaning specified above.

The condensation reaction (i) schematized above, is carried out by reacting the derivative of the β-aminopropionic acid having general formula (IX) with the chloride having general formula (XI), in the presence of an organic solvent and an organic or inorganic base, at a temperature of between –10° C. and the reflux temperature of the solvent used.

Organic solvents which can be used for the purpose are: chlorinated organic solvents such as, for example, dichloromethane, 1,2-dichloroethane; aromatic solvents such as benzene, toluene; ether-type solvents such as diethyl ether, tetrahydrofuran; ester solvents such as ethyl acetate, propyl acetate; mixtures of the above solvents.

Organic bases which can be used for the purpose are, for example, triethylamine, N,N-dimethylaniline.

Inorganic bases which can be used for the purpose are, for example, sodium bicarbonate, potassium bicarbonate.

The chloride having general formula (XI) is, usually, a commercial product or can be easily obtained from the corresponding acid form having general formula (XII):

 (XII)

wherein $R_a$, $K_1$ and W have the same meaning described above, by reaction with a halogenating agent such as, for example, thionyl chloride, phosphorous pentachloride; or, when $K_1$ is oxygen, by treatment of the hydroxylic derivative having general formula (XIII):

 Ra—OH (XIII)

with phosgene, operating according to the processes known in literature.

When the compounds having general formula (Ia) have an $R_a$-$K_1$ group which cannot be obtained by the process described above (i), it is possible to use, instead of the chloride having general formula (XI), the mixed anhydride of the acid having general formula (XII) or the acid itself having general formula (XII). In this case, the condensation reaction (i) is carried out in the presence of a condensation reagent such as, for example, cyclohexylcarbodiimide, carbonyldiimidazol, operating under the same conditions described, for example, in "The Practice of Peptide Synthesis" (1984), pages 7–150, Springer-Verlag Ed.; or, it is also possible to use other methods described in literature relating to the functionalization to nitrogen of aminoacidic or peptidic derivatives such as, for example, those described in "The Practice of Peptide Synthesis" (1984), pages 7–150, Springer-Verlag Ed.

When Q represents a group having general formula (III) and $R_1$, $R_2$ and $R_3$ are hydrogen, the derivative of β-aminopropionic acid having general formula (IX) can be obtained, for example, according to the method described in "Tetrahedron Letters" (1988), Vol. 29, page 6465.

When Q represents a group having general formula (III) and $R_1$, $R_2$ and $R_3$ are hydrogen, or at least one of the substituents among $R_1$, $R_2$ and $R_3$ is different from hydrogen and represents a $C_1$–$C_8$ alkyl or haloalkyl group, linear or branched, the derivative of β-aminopropionic acid having general formula (IX), can be obtained by the opening of the corresponding β-lactam having general formula (XIV):

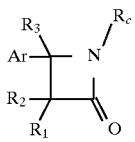 (XIV)

wherein $R_1$, $R_2$, $R_3$ and Rc and Ar have the same meaning described above, with the compound having general formula (XV):

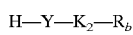 (XV)

wherein Y, $K_2$ and $R_b$ have the same meaning described above, possibly in the presence of an organic base such as, for example, sodium hydride, potassium carbonate; or a mineral acid such as, for example, sulphuric acid, hydrochloric acid; or a Lewis acid such as, for example, zinc chloride, boron trifluoride etherate; or chlorotrimethylsilane; and in the presence or absence of a chlorinated organic solvent such as, for example, dichloromethane, 1,2-dichloroethane; or an aromatic solvent such as, for example, benzene, toluene; or a dipolar aprotic solvent such as, for example, N,N-dimethylacetamide. The above reaction is carried out at a temperature of between –10° C. and 120° C.

The β-lactam having general formula (XIV) can be obtained by the cycloaddition of a suitable olefin and N-chlorosulphonylisocyanate operating according to the method described, for example, in "organic Preparations and Procedures International" (1973), Vol. 5(1), page 13; "Tetrahedron Letters" (1987), Vol. 28, page 227; "Tetrahedron Letters" (1970), Vol.3, page 245; "Tetrahedron Letters" (1977), Vol. 41, page 3643; "Journal of Organic Chemistry" (1984), Vol. 41, page 1397.

The β-lactamic compound having general formula (IXa), when $R_L$ has the same meaning as the group having general formula (IXb), can be prepared from the β-lactam having general formula (XIV), when $R_c$ is hydrogen, by condensation with the chloride (XI), under the conditions described in "Tetrahedron Letters", Vol. 31, page 6429 (1990).

Also when Q represents a group having general formula (III) and $R_2$ is a $C_1$–$C_2$ alkylenic chain which is linked to a carbon atom forming the Ar group, the derivative of β-aminopropionic acid having general formula (IX) can be obtained, for example, by the opening of the corresponding β-lactam having general formula (XIV), operating under the same conditions described above, in turn prepared by the cycloaddition of an indene suitably substituted in the aromatic portion and N-chlorosulphonylisocyanate as described, for example, in "Organic Preparations and Procedures International" (1973), Vol. 5(1), page 13.

When Q represents a group having general formula (III), $R_2$ together with $R_b$ represents a direct bond and $K_2$ is not a direct bond, the derivative of β-aminoproprionic acid having general formula (IX), can be obtained by the addition of a suitable benzylamine having general formula (XVI):

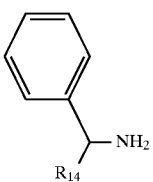 (XVI)

wherein $R_{14}$ represents a $C_1$–$C_8$ alkyl or haloalkyl group, linear or branched, to a β-ketoester having general formula (XVII):

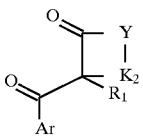 (XVII)

wherein $R_1$, $K_2$, Ar and Y have the same meaning described above, operating under the same conditions described, for example, in "Tetrahedron" (1993), Vol. 49, page 1579.

From the above addition reaction, an imine derivative is obtained having general formula (XVIII):

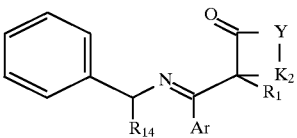 (XVIII)

which is subsequently reduced, for example, by reaction with a borane operating according to the method described, for example, in "Tetrahedron Asimmetry" (1994), Vol. 5, page 1455, to obtain the derivative of β-aminopropionic acid having general formula (IX) wherein $R_c$ is benzyl and $R_3$ is hydrogen.

When $R_1$ is different from hydrogen, the imine derivative having general formula (XVIII), can be added to a lithium derivative having general formula (XIX):

$R_3$—Li (XIX)

wherein $R_3$ has the same meaning described above, in the presence of an ether-type solvent such as, for example, tetrahydrofuran, at a temperature of between –78° C. and –20° C., obtaining the derivative of β-aminopropionic acid having general formula (IX) wherein $R_c$ is benzyl and $R_3$ is different from hydrogen.

Operating with the same procedures described above for β-ketoester having general formula (XVII), it is possible to easily prepare many of the compounds having general formula (I), by the addition of a suitable benzylamine having general formula (XVI) to an appropriate β-ketone having general formula (XX):

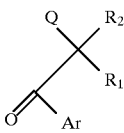 (XX)

In both of the cases described above, if the benzyl group of the amine having general formula (XVI) is optically active, the product obtained will also be optically active as described in the literature specified above. This benzyl group can be easily removed by hydrogenation in the presence of palladium oxide (Pd(OH)$_2$ as catalyst, operating according to the method described, for example, in "Tetrahedron Asimmetry" (1991), Vol. 2, page 183.

A further procedure for obtaining the derivative of β-aminopropionic acid having general formula (IX) in one of the particular cases mentioned above, and in particular in the case wherein $R_5$ is different from hydrogen, consists in the addition of an anion having general formula (XXI):

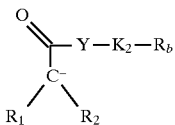

wherein $R_1$, $R_2$, Y, $K_2$ and $R_b$ have the same meaning described above or of one of its equivalent synthon, to an iminic derivative having general formula (XXII):

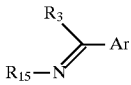

wherein $R_3$ and Ar have the same meaning described above and $R_{15}$ has the same meaning described above for the substituent $R_c$, or represents a benzylic group, to obtain a compound having general formula (XXIII):

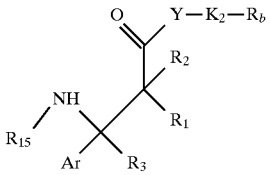

The reaction described above can be carried out operating according to numerous methods described in the art such as, for example, in "Angewandte Chemie" (1989), International Edition, Vol. 28, page 1068; "Tetrahedron Letters" (1991), Vol. 32, page 3151; "Chemical Pharmaceutical Bulletin "(1978), Vol. 26, page 260. This reaction is particularly useful when compounds are to be obtained having general formula (IX) wherein $R_1$ is trifluoromethyl, $R_2$ is hydrogen or a $C_1$–$C_8$ alkyl or haloalkyl group; or compounds having general formula (IX) wherein $R_1$ and $R_2$ are fluorine. These compounds can be obtained in fact using as equivalent synthon to the anion having general formula (XXI), organic zinc described in "Chemistry Letters" (1987), page 1971 or organic zinc described in "Tetrahedron Letters" (1984), Vol. 25, page 2301, respectively.

When a compound is to be obtained having general formula (IX) wherein only one between $R_1$ and $R_2$ is fluorine, it is convenient to use one of the methods described in "Tetrahedron Asymmetry" (1994), Vol. 5, page 955 or in "Tetrahedron Asymmetry" (1994), Vol. 5, page 1005.

When the substituent $R_{15}$ represents a benzylic group, this group can be easily removed by hydrogenation in the presence of palladium oxide (Pd(OH)$_2$) as catalyst, operating according to the method described, for example, in "Tetrahedron Asymmetry" (1991), Vol.2, page 183.

When Q represents a group having general formula (III) and $R_2$ together with $R_3$, represents a $C_1$–$C_8$ alkylenic or haloalkylenic chain, the derivative of β-aminopropionic acid having general formula (IX) can be obtained by the methods described, for example, in "Tetrahedron Letters" (1973), Vol. 38, page 3719.

When Q is a group having general formula (III) and $R_2$ together with $R_1$ represents a $C_1$–$C_8$ alkylenic or haloalkylenic chain, the derivative of β-aminopropionic acid having general formula (IX) can be obtained with the methods described, for example, in "Tetrahedron Letters" (1973), Vol. 38, page 3719, "Journal of Organic Chemistry" (1970), Vol. 35, page 2043, "Journal of Organic Chemistry" (1985), Vol. 50, page 169.

When Q represents a group having general formula (III) and $R_5$ represents a $C_1$–$C_2$ alkylenic chain which is joined to a carbon atom forming the Ar group, the derivative of β-aminopropionic acid having general formula (IX) can be obtained, for example, by means of the following reaction scheme (ii):

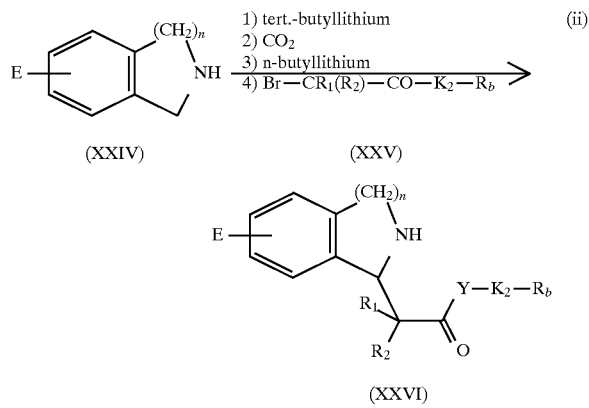

The reaction (ii) sketched above, is carried out by reacting the amine having general formula (XXIV) wherein E represents one of the possible substituents previously defined for a phenyl group optionally substituted, n is an integer between 1 and 2, with tert.-butyllithium and carbon dioxide, then with a mole of n-butyllithium and finally alkylated with the bromide having general formula (XXV) wherein $R_1$, $R_2$, Y, $K_2$ and $R_b$ have the meaning described above, operating under the conditions described in "Tetrahedron Letters" (1986), Vol. 42, page 2571.

When Q represents a group having general formula (III) and $R_2$ together with $R_5$ represents a $C_1$–$C_8$ alkylenic or haloalkylenic chain, the derivative of β-aminopropionic acid having general formula (IX) can be obtained, for example, with the method described in "Tetrahedron Asymmetry" (1994), Vol. 5, page 1455.

Any derivative of β-aminopropionic acid having general formula. (IX) wherein $R_c$ is different from hydrogen, can be obtained from any compound having general formula (IX) wherein $R_c$ is hydrogen obtained, in turn, with any of the methods described above, protecting the nitrogen atom with the tert.-butylbenzyloxycarbonyl group by reaction with a base such as, for example, potassium tert.-butylate, and with a halide having general formula (XXVII):

wherein $R_5$ has the same meaning described above and Alog. is a halogen atom selected from iodine or bromine, operating under the same conditions described in "Journal of Organic Chemistry" (1989), Vol. 54, page 617.

When Q represents a cyano group, the derivative of β-aminopropionic acid having general formula (IX) can be obtained, for example, with the method described in "Tetrahedron Letters" (1990), Vol. 31, page 6379; or it can be obtained from the corresponding compounds having general formula (IX) wherein Q represents the group having general formula (III), by simply transforming the same group into amide and dehydrating this, operating with one of the many methods described in literature.

When Q represents a thiazolic group, the derivative of β-aminopropionic acid having general formula (IX) can be obtained from the corresponding compounds having general formula (IX) wherein Q represents the group having general formula (III), by simply transforming the same group into amide and dehydrating this operating, for example, as described in "Synthetic Communications" (1990), Vol. 20, page 2235, or in "Tetrahedron Letters" (1990), Vol. 46, page 8267.

Similarly, if in the desired derivative of β-aminopropionic acid having general formula (IX), Q represents a group having general formula (III) wherein the group Y—$K_2$—$R_b$ is not compatible with the preparative method selected, it is easy to prepare the derivative having general formula (IX) wherein the group Y—$K_2$—$R_b$ represents —O—$CH_2$—Ph (Ph=phenyl) or —O—$C(CH_3)_3$ which, at the end of the reaction, can be easily removed, by, respectively, hydrogenation and by treatment with acids so as to obtain the corresponding acid of the derivative having general formula (IX) wherein Y—$K_2$—$R_b$ represents OH. This acid can then be easily transformed into the desired group having general formula (III) using one of the numerous methods described in literature such as, for example, in "The Practice of Peptide Synthesis" (1984), pages 89–150, Springer-Verlag Ed., after possible protection of the aminic group with, for example, groups which can be easily removed such as tert.-butoxycarbonyl and benzyloxycarbonyl, operating with the methods described, for example, in "The Practice of Peptide Synthesis" (1984), pages 89–150, Springer-Verlag Ed.

When Z represents an AA aminoacid residue, the compounds having general formula (Ib):

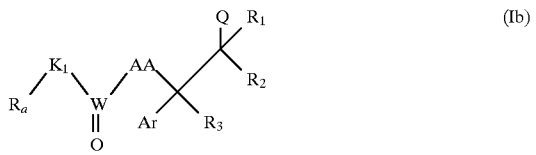

wherein $R_1$, $R_2$, $R_3$, $R_a$, $K_1$, W, Ar, Q and AA have the same meaning described above, can be obtained by reacting the chloride having general formula (XI), described above, with a suitable aminoacid having general formula (XXVIII):

or with its trimethylsilicic ester having general formula (XXIX):

wherein AA represents an aminoacidic residue having general formula (VI) wherein L is, in this case, equal to oxygen, in the presence of a base such as,. for example, triethylamine, N,N-dimethylaniline, sodium or potassium bicarbonate and a chlorinated or dipolar aprotic solvent such as, for example, those previously mentioned, operating at a temperature of between −10° C. and the reflux temperature of the solvent used.

When the aminoacid having general formula (XXVIII) is used it is possible to carry out the reaction in water.

The above reaction takes place according to the following scheme (iii):

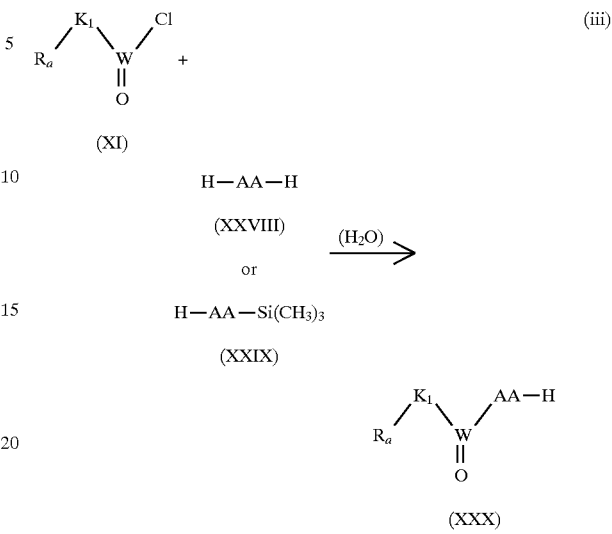

The aminoacid having general formula (XXX), obtained by means of the reaction (iii) shown above, is in turn reacted with the derivative of β-aminopropionic acid having general formula (IX) operating under the same conditions described above for the reaction diagram (i).

The compounds having general formula (I) have a particularly fungicidal activity against phytopathogen fungi which attack cultivations of vines, sugarbeet, cereals, Cucurbitaceae and fruit trees.

Plant diseases which can be fought with the compounds having general formula (I) of the present invention are, for example, the following:

Plasmopara viticola on vines;
Sphaerotheca fuliginea on Cucurbitaceae;
Phythium on vegetables;
Phytophthora spp. on vegetables;
Helminthosporium teres on cereals;
Erisyphe graminis on cereals;
Puccinia spp. on cereals;
Septoria spp. on cereals;
Rhynchosporiun on cereals;
Podosphera leucotricha on cereals;
Uncinula necator on vines;
Venturia spp. on fruit;
Pyricularia oryzae on rice;
Botrytis cinerea;
Fusarium spp. on cereals; etc.

The compounds having general formula (I) are capable of carrying out a fungicidal activity which is both curative and preventive and, in addition, they have a very limited or no phytotoxicity at all.

For practical use in agriculture it is often useful to use fungicidal compositions containing one or more compounds having general formula (I), possibly also as a mixture of isomers, as active substance.

The application of these compositions can be on any part of the plant, for example on the leaves, stalks, branches and roots, or on the seeds themselves before being planted, or also on the soil where the plant grows.

Compositions can be used which are in the form of dry powders, wettable powders, emulsionable concentrates, micro-emulsions, pastes, granules, solutions, suspensions, etc: the selection of the type of composition depends on the specific use.

The compositions are prepared in the known way, for example by diluting or dissolving the active substance with a solvent and/or solid diluent, possibly in the presence of surface-active agents.

Solid diluents or supports which can be used are: silica, kaolin, bentonite, talc, infusorial earth, dolomite, calcium carbonate, magnesia, chalk, clays, synthetic silicates, attapulgite, sepiolite.

As liquid diluents, apart from water of course, various solvents can be used, for example aromatics (xylols or mixtures of alkylbenzols), chloroaromatics (chlorobenzol), paraffins (petroleum fractions), alcohols (methanol, propanol, butanol, octanol, glycerine), amines, amides (N,N-dimethylformamide, N-methylpyrrolidone), ketones (cyclohexanone, acetone, acetophenone, isophorone, ethylamylketone), esters (isobutyl acetate).

Surface-active agents which can be used are salts of sodium, calcium, triethanolamine or triethylamine of alkylsulphonates, alkylarylsulphonates, polyethoxylated alkylphenols, fatty alcohols condensed with ethylene oxide, polyoxyethylated fatty acids, esters of polyoxyethylated sorbitol, lignin sulphonates.

The compositions can also contain special additives for particular purposes such as, for example, adhesion agents, such as arabic rubber, polyvinyl alcohol, polyvinylpyrrolidone.

If desired, it is also possible to add other compatible substances to the compositions of the present invention such as, for example, fungicides, phytoregulators, antibiotics, weed-killers, insecticides, fertilizers.

Examples of fungicides which can be included in the composition of the invention are alanicarb, ampropylfos, anilazine, azaconazol, BAS 490 F, benomyl, biloxazol, binapacryl, bitertanol, blasticidine S, bromoconazol, bupyrimate, butenachlor, butiobate captafol, captan, carbendazim, carboss, quinoethionate chlorobenzothiazone, cloroneb, chlorothalonyl, clozolinate, clozylacon, copper salts, cyclohexyimide, cymon- axyl, cyproconazol, cyprofuran, diclofuanid, diclone diclobutrazol, diclomezine, dicloran, didecyl- or dimethyl-ammonium chloride, dietophencarb, dipheconazol, dimefluazol-, dimethconazol, dimethomorph, dimethyrimol, diniconazol, dinocap, dipyrition, dithalimphos, dithianon, dodemorph, dodine, doguadine, ediphenphos, epoxyconazol, ethconazol, ethyrimol, ethoxyquin, ethridiazol, fenaminosulf, fenapanyl, fenarimol, fenbuconazol, fenfuran, fenpiclonyl, fenpropidin, fenpropimorph, fentin acetate, ferbam, fluazinam, fluoroimide, fluotriamzol, flutolanyl, flutriafol, fluzylazol, folpet, fuberidazol, furalaxyl, cis-furconazol, guazatine, ICI A 5504, hydroxyisooxazol, imesazol, imazalyl, imibenconazol, ipconazol, iprobenfos, iprodion, isoprotiolan, kasugamycin, mancozeb, maneb, mepanipyrim, mepronyl, metalaxyl, metconazol, metfuroxam, metiram, metsulfovax, myclobutanyl, neoasozin, nuarimol, ofurax, oxadixyl, oxycarboxyn, perfurazoate, penconazol, pencycuron, phenazine oxide, fosetyl-Al, phosphoric acids, phthalide, polyoxin D, polyram, probenazol, procloraz, procimidone, propamocarb, propiconazol, propineb, propionic acid, protiocarb, pyracarbolid, pyrazofos, pyriphenox, pyroquilon, pyroxyfur, pyrrolnitrin, compounds containing quaternary ammonium, quinconazol, quinomethionate, quintozene, rabenazol, sodium pentachlorophenate, SSF 126, SSF 129, streptomycin, sulphur, tebuconazol, teclophthalam, tecnazene, thyabendazol, thycarbanyl, thyciophen, 2-(thiocyanomethylthio)benzothiazol, methyl-thiophanate, tiram, thymibenconazol, methyl-thyclophos, tolylfluanid, triacetate salt of 1,1'-imino-di(octamethylene)diguanidine, triadimephon, triadimenol, triazabutyl, triazaoxide, tricyclazol, tridemorf, triforin, triflumizol, trithyconazol, validamycin A, vapam, vinclozolin, zineb and ziram.

The concentration of active substance in the above compositions can vary within a wide range, depending on the active compound, the crop, the pathogen, the environmental conditions and type of formulation adopted.

In general the concentration of active substance varies between 0.1% and 95%, preferably between 0.5% and 90%.

The examples hereunder are illustrative and do not limit the present invention.

Tables 1–11, 13–18, 25 and 29 provide examples of compounds having general formula (I) whereas Tables 12, 19, 24 and 26–28 give examples of compounds having general formula (IX) and Tables 20–23 give examples of compounds having general formula (IXa).

Table 30 illustrates the elemental analysis of the synthesized compounds.

EXAMPLE 1

Synthesis of (±) isopropyl N-(2,2-dichloro-l-methylcyclopropylcarbonyl)-3-phenylpropionate (Compound Nr. 1.1).

1.9 g of 2,2-dichloro-1-methylcyclopropylcarboxylic acid are suspended in 20 cm$^3$ of methylene chloride.

2.68 g of isopropyl 3-amino-3-phenylpropionate and 1.11 g of triethylamine are added and the whole mixture is then cooled to 0° C. and 2.8 g of cyclohexylcarbodiimide are added. The temperature is left to rise to environmental values and, after 1 hour at room temperature, the solvent is evaporated under vacuum.

The raw reaction product obtained is directly purified on silica gel using hexane/ethyl acetate in a ration of 8/2 as eluant.

2.9 g of the desired compound are obtained with a yield of 67%.

EXAMPLE 2

Operating with the same procedure described in example 1, the other compounds having general formula (I) and shown in Tables 1–3, were prepared.

EXAMPLE 3

Synthesis of isopropylic ester of N-(tert.-butyloxycar- bonyl)-L-valinyl-DL-β-phenyl-α-methyl-β-alanine (Compound Nr. 4.1).

1.1 g of cyclohexylcarbodiimide are added to a solution, cooled to 0° C., obtained by mixing 0.9 g of tert.- butyloxycarbonyl-L-valine, 1.3 g of isopropyl 3-phenyl-3-amino-2-methylpropanoatehydrochlorate (corresponding to β-phenyl-α-methyl-β-alanine) and 0.46 g of triethylamine in 10 cm³ of methylene chloride.

After 1 hour at room temperature, the solution is evaporated at reduced pressure and the raw reaction product obtained is directly purified on silica gel using hexane/ethyl acetate in a ration of 7/3 as eluant.

1.4 g of the desire compound are obtained with a yield of 75%.

EXAMPLE 4

Operating with the same procedure described in example 3, the other compounds having general formula (I) and shown in Tables 4–11, were prepared.

EXAMPLE 5

Sythesis of DL-β-phenyl-β-alanine (corresponding to 3-phenyl-3-aminopropanoic acid) (Compound Nr. 12.1)

A suspension of 100 g of benzaldehyde, 94 g of malonic acid, 109 g of ammonium acetate in 300 cm³ of ethanol, is brought to boiling point in a nitrogen atmosphere, under vigorous stirring. The suspension is mantained under the above conditions for about eight hours.

The suspension is then cooled to 20° C. and the white crystalline solid precipitate is filtered. The white crystalline solid thus obtained is washed twice with ethyl ether (200 cm³ for each washing).

After drying under vacuum in the presence of phosphoric anhydride, 90 g of the desired compound are obtained with a yield of 58%, and with a melting point equal to 229° C.

EXAMPLE 6

Operating with the same procedure described in example 5, the other compounds having general formula (I) and shown in Tables 12, were prepared.

EXAMPLE 7

Preparation of N-(4-methoxyphenyl)-3,3-dimethyl-4-phenylazetidin-2-one (Compound Nr. 21.2)

26.8 g of ethyl isobutyrate are added at −78° C. to a solution of 27.5 g of lithium isopropylamide, prepared in situ by adding 160 cm³ of n-butyllithium (1.6M solution in hexane) to a solution of 25.7 g of diisopropylamine in 100 cm³ of anhydrous tetrahydrofuran. After about 60 minutes a solution of 48.8 g of N-(4-methoxyphenyl)benzaldimine in 480 cm³ of anhydrous tetrahydrofuran are slowly added dropwise, maintaining the temperature at −78° C. for a further 90 minutes. The temperature is left to slowly rise and the mixture is left under stirring for a night. The solvent is evaporated, and ethyl acetate and a solution of aqueous acetic acid at 10% are added. The organic phase is washed with water, dried on sodium sulphate, and is then evaporated. The raw product is purified on silica gel, using a mixture of ethyl acetate/hexane as eluant in a ratio of 2/8 and 33.4 g of N-(4-methoxyphenyl)-3,3-dimethyl-4-phenylazetidin-2-one are obtained (yield 52%).

EXAMPLE 8

Preparation of 3,3-dimethyl-4-phenylazetidin-2-one (Compound Nr. 20.4).

A solution of 24.4 g of N-(4-methoxy-phenyl)-3,3-dimethyl-4-phenylazetidin-2-one and 16.5 g of lithium 25 perchlorate in a mixture of 500 cm³ of acetonitrile and 50 cm³ of water, is subjected to electrolysis in a unseparated cell, using a graphite anode and a stainless steel grille as cathode and maintaining a constant potential difference of 1.5 V. At the end of the reaction the solution is concentrated to ¼ of volume. An extraction is made with ethyl acetate and the organic phase is washed with a solution of aqueous sodium sulphite at 10% and then with water; it is dried with sodium sulphate and then evaporated. The raw product is purified on silica gel, using a mixture of ethyl acetate/hexane as eluant in a ratio of 3/7 and 15.4 g of 3,3-dimethyl-4-phenylazetidin-2-one are obtained (yield (98%).

EXAMPLE 9

Preparation of 4-phenylazetidin-2-one (Compound Nr. 20.1)

40 g of styrene are slowly dripped into a solution of 54 g of chlorosulphonylisocyanate in 80 cm³ of ethyl ether, maintaining the solvent at reflux temperature. After three hours the reaction mixture is cooled and is added in small quantities to a solution of 48 g of sodium sulphite in 195 cm³ of water, maintaining the temperature at less than 22° C. with an external ice bath and the pH within a range of between 7 and 8 by adding an aqueous solution of potassium hydroxide at 10%. At the end of the addition the mixture is filtered and the organic phase of the filtrate is dried on sodium sulphate and evaporated. 21 g of the desired compound are obtained (yield 38%).

EXAMPLE 10

Using the same methods described in examples 7, 8 and 9, the other compounds listed in tables 20, 21 and 23 were also prepared.

EXAMPLE 11

Preparation of methyl ester of 3-phenyl-3-amino-2,2-dimethylpropanoic acid (Compound Nr. 19.14)

A solution of 15.4 g of 3,3-dimethyl-4-phenylazetidin-2-one and 14.3 g of chlorotrimethylsilane in 150 cm³ of anhydrous methanol are refluxed for 6 hours. The solution is then evaporated and ethyl acetate and aqueous sodium bicarbonate at 5% are added. The organic phase is washed with water, is dried on sodium sulphate, and is then evaporated, obtaining 17.8 g of methyl 3-phenyl-3-amino-2,2-dimethylpropanoate (yield 98%).

EXAMPLE 12

Preparation of the tert.-butylic ester of 3-amino-3-phenylpropionic acid (Compound Nr. 12.14).

A solution of 10 g of 4-phenylazetidin-2-one and 15.2 g of chlorotrimethylsilane in 150 cm³ of anhydrous tert.-butanol are refluxed for 7 days. The solution is then evaporated and ethyl acetate and aqueous sodium bicarbonate at 5% are added. The organic phase is washed with water, dried on sodium sulphate and is then evaporated. 7 g of tert.-butyl 3-phenyl-3-amino-propanoate are obtained (yield 47%).

EXAMPLE 13

Preparation of N-methyl amide of 3-amino-3-phenylpropionic acid (Compound Nr. 19.24)

40 cm³ of an aqueous solution of N-methylamine at 40% are added to a solution of 4 g of 4-phenylazetidin-2-one in 40 cm³ of tetrahydrofuran. After 5 days at room temperature, the solvents are evaporated, and dichloromethane is added. The mixture is dried on sodium sulphate, the solvent is evaporated and 4.7 g of the desired product are obtained (yield 98%).

EXAMPLE 14

Preparation of the isopropylic ester of 3-amino-3-phenylpropionic acid (Compound Nr. 12.15).

14.3 g of thionyl chloride are slowly added to a suspension of 20 g of 3-amino-3-phenylpropionic acid in 400 cm³ of anhydrous isopropanol and the solution is then brought to reflux temperature for three hours. (Alternatively it is possible to substitute the thionyl chloride with gaseous hydrochloric acid with which the alcohol solution is saturated). The solvent is evaporated and ethyl acetate and aqueous sodium bicarbonate at 5% are added to the raw product. The organic phase is washed with water, dried on sodium sulphate, and then evaporated. 24.9 g of the desired product are obtained (yield 99%).

EXAMPLE 15

The products indicated in Tables 19 and 26 were obtained with the same procedures described in examples 11, 12, 13 and 14.

EXAMPLE 16

Preparation of the methyl ester of N-(N-phenoxycarbonyl)-L-valinyl-DL-β-phenyl-α,α-dimethyl-β-alanine (alsomethyl3-(N-(N-phenoxycarbonylvalinyl)amino)-2,2-dimethyl-3-phenylpropanoate) (Compound Nr. 16.8)

8.6 g of N-methylmorpholine and subsequently 11.6 g of isobutyl chloroformate are added to a solution of 20 g of N-phenoxycarbonyl-L-valine in 150 cm³ of anhydrous THF at −30° C. After 10 minutes a solution of 17.6 g of methyl 3-phenyl-3-amino-2,2-dimethylpropanoate in 40 cm³ of anhydrous THF is added, and the mixture is subsequently maintained under stirring at −30° C. for 60 minutes and the temperature is then left to rise to room values. The solvent is evaporated, and ethyl acetate and a solution of aqueous sodium chloride at 10% are added. The organic phase is washed with water, is dried on sodium sulphate, and is then evaporated. The raw product is purified on silica gel, using a mixture of ethyl acetate/hexane as eluant in a ratio of 2/8 and 33.3 g of compound Nr. 16.8 are obtained (yield 92%).

EXAMPLE 17

The products listed in Tables 16, 17, 18, 25 and 29 were prepared using the same method described in examples 3 and 16.

EXAMPLE 18

Preparation of the isopropylic ester of 3-[N-(2,2-dichloro-1-methyl-3-ethylcyclopropylcarbonyl)]amino-3-phenylpropionic acid (Compound Nr. 13.12).

1.4 g of the chloride of 2,2-dichloro-1-methyl-3-ethylcyclopropylcarboxylic acid (obtained according to the methods described in U.S. Pat No. 5,117,053 or U.S. Pat. No. 4,988,734) are added to a solution of 1.6 g of 3-amino-3-phenylpropionic acid and 0.77 g of triethylamine in 10 cm³ of methylene chloride, the temperature being maintained at about 0° C. The mixture is left under stirring for about 4 hours, the solvent is then evaporated and ethyl acetate and a solution of aqueous sodium chloride at 10% are added. The organic phase is washed with water, dried on sodium sulphate and is then evaporated. The raw product is purified on silica gel using a mixture of ethyl acetate/hexane as eluant in a ratio of 2/8 and 2 g of compound Nr. 13.12 are obtained (yield 67%).

EXAMPLE 19

The products listed in Table 13 were prepared using the same method described in example 18.

EXAMPLE 20

Preparation of 3-[N-(4-methoxyphenyl)]amino-3-phenyl-2,2-dimethylpropanoic acid (Compound Nr. 27.1).

13.13 g of caustic soda are added to a solution of the methyl ester of 3-[N-(4-methoxyphenyl)]amino-3-phenyl-2,2-dimethylpropanoic acid (compound Nr. 19.3) in 30 cm³ of methanol. The mixture is refluxed for 12 hours and the solvent is then removed by distillation at reduced pressure. 0.4 g of the crude sodium salt of the desired acid are obtained. Alternatively, it is possible to treat the ester with hydrochloric acid 36N, maintaining the whole mixture at reflux temperature for 12 hours and obtaining the corresponding hydrochloride. The sodium salt or hydrochloride are purified by elution on resin. Yield 75%.

EXAMPLE 21

The products listed in Table 27 were prepared using the same method described in example 20.

EXAMPLE 22

Preparation of 1-amino-1-phenyl-2-(4,5-dimethylthiazol-2-yl)ethane; Compound Nr.24.1 a) A solution of 5 g of 2,4,5-trimethylthiazol in 10 cm³ of anhydrous THF is added at −78° C. to a solution of 4.6 g of lithium isopropylamide, prepared in situ by adding 27 cm³ of n-butyllithium (1.6 M solution in hexane) to a solution of 4.35 g of diisopropylamine in 60 cm³ of anhydrous THF. After about 60 minutes a solution of 5.26 g of benzonitrile in 50 cm³ of anhydrous THF is slowly added dropwise, the temperature being maintained at −78° C. for a further 90 minutes. The temperature is left to rise slowly and the mixture is then left under stirring for a night. The solvent is evaporated, and ethyl acetate is added. The organic phase is washed with water, dried on sodium sulphate and is then evaporated. The raw product is purified on silica gel, using a mixture of ethyl acetate/hexane as eluant in a ratio of 3/7. 6.8 g of 1-amino-1-phenyl-2-(4,5-dimethylthiazol-2-yl) ethylene are obtained (yield 76%).

b) A 2 N hydroalcoholic solution of hydrochloric acid is added to a solution of 3 g of 1-amino-1-phenyl-2-(4,5-dimethylthiazol-2-yl)ethylene in 100 cm³ of methanol and containing a green trace of bromocresol, until the colour changes from night-blue to yellow-orange. 0.82 g of sodiumcyanoboride are added under vigorous stirring, the acid solution being maintained by the addition of the hydroalcoholic hydrochloric solution. After an hour at room temperature, the solvent is evaporated, water is added, which is washed with ethyl ether. The aqueous phase is then basified with sodium hydroxide and extracted with ethyl acetate. It is dried on sodium sulphate and the solvent is evaporated. 1.5 g of 1-amino-1-phenyl-2-(4,5-diemthylthiazol-2-yl)ethane are obtained (yield 50%).

EXAMPLE 23

The products listed in Table 24 were prepared using the same method described in example 22.

EXAMPLE 24

Determination of the preventive fungicidal activity against vine mildew (Plasmopara viticola).

Plant leaves of the cultivar Dolcetto vine, grown in vases in a conditioned environment (20°±1° C., 70% relative humidity), are treated by spraying both sides of the leaf with the compounds indicated in Tables 1–29 in a hydroacetonic solution at 20% by volume in acetone.

After remaining 24 hours in a conditioned environment the plants are sprayed on both sides of the leaf with an aqueous suspension of conidia of Plasmopara viticola (200000 conidia per cm$^3$).

The plants are maintained in a humidity saturated environment, at 21° C., for the incubation period of the fungus.

At the end of this period (7 days), the fungicidal activity is evaluated according to a percentage evaluation scale from 100 (healthy plant) to 0 (completely infected plant).

All the synthesized compounds showed a control of more than 90, at the concentration used of 2000 ppm.

EXAMPLE 25

Determination of the preventive fungicidal activity against cucumber mildew (Sphaerotheca fuliginea)

Leaves of cultivar Marketer cucumber plants, grown in vases in a conditioned environment (20°±1° C., 70% relative humidity), are treated by spraying both sides of the leaf with the compounds indicated in Tables 1-29 in a hydroacetonic solution at 20% by volume in acetone.

After remaining 24 hours in a conditioned environment the plants are sprayed on both sides of the leaf with an aqueous suspension of conidia of Sphaerotheca fuliginea (200000 conidia per cm$^3$).

The plants are maintained in a humidity saturated environment, at 21° C., for the incubation period of the fungus.

At the end of this period (8 days), the fungicidal activity is evaluated according to a percentage evaluation scale from 100 (healthy plant) to 0 (completely infected plant).

All the synthesized compounds showed a control of more than 90, at the concentration used of 2000 ppm.

TABLE 1

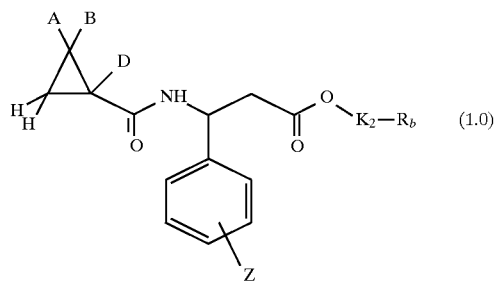

Compounds having formula (I) wherein: $R_1$, $R_2$ and $R_3$ are hydrogen; $K_1$ is a direct bond; $R_a$ is cyclopropane; W is carbon; Y is oxygen.

| COMP. Nr | A | B | D | E | $K_2-R_b$ |
|---|---|---|---|---|---|
| 1.1 | Cl | Cl | $CH_3$ | — | $CH(CH_3)_2$ |
| 1.2 | Cl | Cl | $CH_3$ | — | $CH_2Ph^*$ |
| 1.3 | Cl | Cl | $CH_3$ | 4-$OCH_3$ | $CH(CH_3)_2$ |
| 1.4 | Cl | Cl | $CH_3$ | 4-Cl | $CH(CH_3)_2$ |
| 1.5 | Cl | Cl | $CH_3$ | 3,4-MDO** | $CH(CH_3)_2$ |
| 1.6 | Cl | Cl | $CH(CH_3)_2$ | — | $CH(CH_3)_2$ |
| 1.7 | H | H | H | — | $CH(CH_3)_2$ |
| 1.8 | H | H | Ph* | — | $CH(CH_3)_2$ |
| 1.9 | Cl | Cl | $CH_3$ | — | $CH_3$ |
| 1.10 | Cl | Cl | Cl | — | $C(CH_3)_3$ |
| 1.11 | Cl | Cl | $CH_3$ | 4-F | $CH_3$ |

*phenyl
**3,4-methylenedioxy

TABLE 2

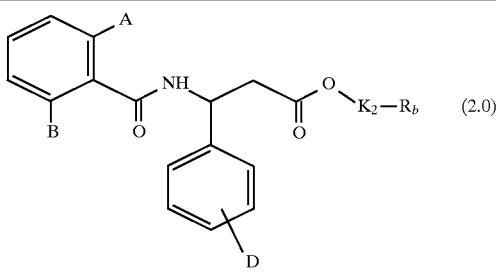

Compounds having formula (I) wherein: $R_1$, $R_2$ and $R_3$ are hydrogen; $K_1$ is a direct bond; $R_a$ is phenyl; Ar is phenyl; Y is oxygen

| COMP. Nr | A | B | D | $K_2-R_b$ |
|---|---|---|---|---|
| 2.1 | Cl | Cl | — | $CH(CH_3)_2$ |
| 2.2 | Cl | H | — | $CH(CH_3)_2$ |
| 2.3 | Cl | Cl | 4-$CF_3$ | $CH(CH_3)_2$ |

TABLE 3

(3.0)

Compounds having formula (I) wherein: $R_a-K_1-W(=O)-$ is BOC (tert.-butyloxycarbonyl); Z is $N-R_5$; Ar is phenyl; $R_3$ is hydrogen.

| COMP. Nr | $R_1$ | $R_2$ | $R_5$ | E | $K_2-R_b$ | Y |
|---|---|---|---|---|---|---|
| 3.1 | H | H | H | — | $CH(CH_3)_2$ | O |
| 3.2 | H | H | $CH_3$ | — | $CH(CH_3)_2$ | O |
| 3.3 | H | H | H | — | $CH(CH_3)_2$ | NH |
| 3.4 | H | H | H | — | $CH(CH_3)_2$ | [Val]—O |
| 3.5 | H | $CH_3$ | H | — | $CH(CH_3)_2$ | O |
| 3.6 | $CH_3$ | $CH_3$ | H | — | $CH(CH_3)_2$ | O |
| 3.7 | $CH_3$ | $CH_3$ | H | — | $CH(CH_3)_2$ | NH |

TABLE 4

(4.0)

Compounds having formula (I) wherein: $R_a-K_1-W(=O)-$ is BOC (tert.-butyloxycarbonyl); Z is AA; Ar is phenyl; Y is oxygen.

| COMP. Nr | $R_1$ | $R_2$ | $R_3$ | AA | E | $K_2-R_b$ |
|---|---|---|---|---|---|---|
| 4.1 | H | $CH_3$ | H | [Val]—NH | — | $CH(CH_3)_2$ |
| 4.2 | $CH_3$ | $CH_3$ | H | [Val]—NH | — | $CH(CH_3)_2$ |
| 4.3 | H | $CH_3$ | $CH_3$ | [Val]—NH | — | $CH(CH_3)_2$ |
| 4.4 | H | H | H | [Val]—NH | — | $-CH_3$ |
| 4.5 | H | H | H | [Val]—NH | — | $-CH_2CH_3$ |
| 4.6 | Me | Me | H | [Val]—NH | — | $-CH_3$ |
| 4.7 | Me | Me | H | [Val]—NH | — | $-CH_2CH_3$ |
| 4.8 | $CH_3$ | $CH_3$ | H | [Leu]—NH | — | $-CH_3$ |
| 4.9 | H | H | H | [Val]—NH | — | $C(CH_3)_3$ |
| 4.10 | H | H | H | [Val]—NH | 4-Cl | $-CH_3$ |
| 4.11 | H | $CH_3$ | H | [Val]—NH | — | $-CH_3$ |
| 4.12 | H | $CH_3$ | H | [Val]—NH | — | $-CH_2CH_3$ |
| 4.13 | H | $CH_3$ | H | [Val]—NH | 4-$OCH_3$ | $-CH_3$ |
| 4.14 | H | H | H | [Val]—NH | 4-CN | $CH(CH_3)_2$ |
| 4.15 | H | H | H | [Val]—NH | 4-CN | $CH_2CH_3$ |
| 4.16 | $CH_3$ | $CH_3$ | H | [Val]—NH | 4-CN | $-CH_3$ |
| 4.17 | H | H | H | [Val]—NH | 4-F | $CH(CH_3)_2$ |
| 4.18 | H | H | H | [Val]—NH | 4-Cl | $CH(CH_3)_2$ |
| 4.19 | H | H | H | [Val]—NH | 4-Me | $CH(CH_3)_2$ |

TABLE 4-continued

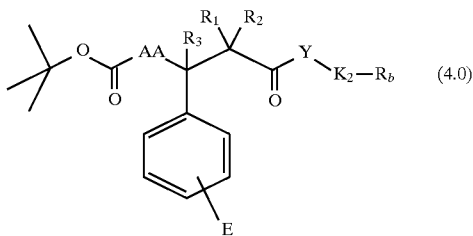

Compounds having formula (I) wherein: $R_a-K_1-W(=O)-$ is BOC (tert.-butyloxycarbonyl); Z is AA; Ar is phenyl; Y is oxygen.

| COMP. Nr | $R_1$ | $R_2$ | $R_3$ | AA | E | $K_2-R_b$ |
|---|---|---|---|---|---|---|
| 4.20 | H | H | H | [Val]—NH | 4-Ethyl | $CH(CH_3)_2$ |
| 4.21 | H | H | H | [Val]—NH | 4-$CF_3$ | $CH(CH_3)_2$ |
| 4.22 | H | H | H | β[Ala]NH | — | $CH(CH_3)_2$ |
| 4.23 | H | H | H | [Val]—NH | 4$OCF_2CF_2H$ | $CH(CH_3)_2$ |
| 4.24 | H | H | H | [Val]—NH | 4$OCH(CH_3)_2$ | $CH(CH_3)_2$ |
| 4.25 | H | H | H | [Val]—NH | 4$OCH_2Ph$** | $CH(CH_3)_2$ |
| 4.26 | H | H | H | [Val]—NH | 4-O-⬡ | $CH(CH_3)_2$ |
| 4.27 | H | H | H | [CPA]*NH | — | $CH(CH_3)_2$ |
| 4.28 | H | H | H | [3AB]***NH | — | $CH(CH_3)_2$ |
| 4.29 | H | H | H | [Val]—NH | 3OMe;4OMe | $CH(CH_3)_2$ |
| 4.30 | H | H | H | [Val]—NH | 2Cl;4OMe | $CH(CH_3)_2$ |
| 4.31 | H | H | H | [Val]—NH | 2-Cl | $CH(CH_3)_2$ |
| 4.32 | H | H | H | [Val]—NH | 3-$CF_3$ | —$CH_3$ |

*[CPA] = cis-2-aminocyclopentylcarbonyl
**Ph = phenyl
***[3AB] = 3-aminobutanoyl

TABLE 5

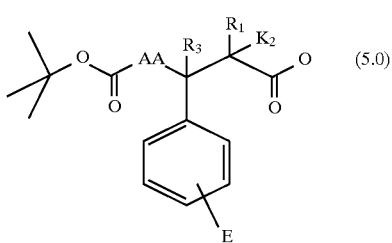

Compounds having formula (I) wherein: $R_a-K_1-W(=O)-$ is BOC (tert.-butyloxycarbonyl); Z is AA; Ar is phenyl; $R_2$ and $R_b$ form a direct bond.

| COMP. Nr | $R_1$ | $R_3$ | $K_2$ | AA | E |
|---|---|---|---|---|---|
| 5.1 | H | H | $(CH_2)_2$ | [Val]—NH | — |
| 5.2 | H | H | $(CH_2)_2$ | [Val]—NH | 4-$OCH_3$ |

TABLE 6

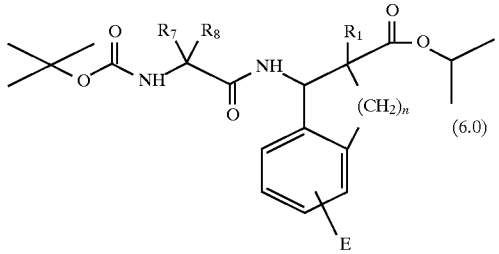

Compounds having formula (I) wherein: $R_a-K_1-W(=O)-$ is BOC (tert.-butyloxycarbonyl); Z is AA; Ar is phenyl; $R_2$ is a $C_1$-$C_2$ alkylenic chain joined to a carbon atom forming the Ar group; $R_9$ is hydrogen.

| COMP. Nr | $R_1$ | $R_7$ | $R_8$ | n | E |
|---|---|---|---|---|---|
| 6.1 | H | H | $CH(CH_3)_2$ | 1 | — |
| 6.2 | H | H | $CH(CH_3)_2$ | 1 | — |
| 6.3 | H | $CH_3$ | $CH_3$ | 1 | — |

TABLE 7

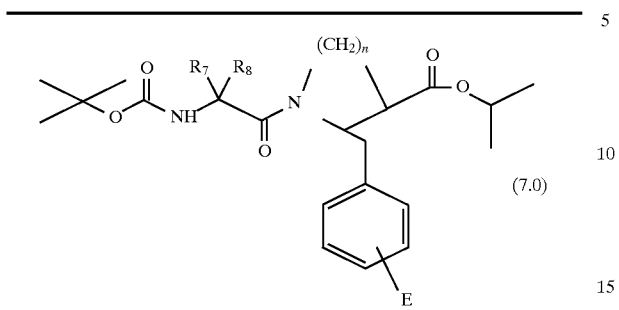

(7.0)

Compounds having formula (I) wherein: $R_a-K_1-W(=O)-$ is BOC (tert.-butyloxycarbonyl); Z is AA; G is a direct bond; Ar is phenyl; $R_9$ together with $R_2$ represents a $C_1-C_8$ alkylenic chain.

| COMP. Nr | $R_1$ | $R_7$ | $R_8$ | n | E |
|---|---|---|---|---|---|
| 7.1 | H | H | $CH(CH_3)_2$ | 2 | — |
| 7.2 | H | H | $CH(CH_3)_2$ | 3 | — |

TABLE 8

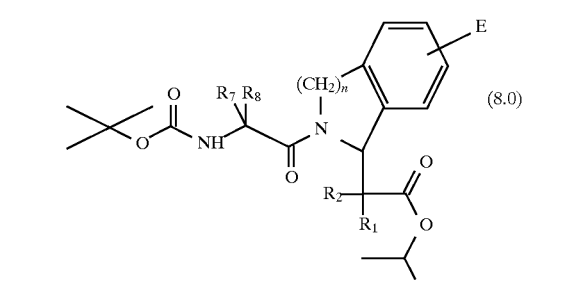

(8.0)

Compounds having formula (I) wherein: $R_a-K_1-W(=O)-$ is BOC (tert.-butyloxycarbonyl); Z is AA; G is a direct bond; Ar is phenyl; $R_9$ is a $C_1-C_2$ alkylenic chain joined to a carbon atom of the substituent Ar.

| COMP. Nr | $R_1$ | $R_2$ | $R_7$ | $R_8$ | n | E |
|---|---|---|---|---|---|---|
| 8.1 | H | H | H | $CH(CH_3)_2$ | 1 | — |
| 8.2 | H | H | H | $CH(CH_3)_2$ | 2 | — |

TABLE 9

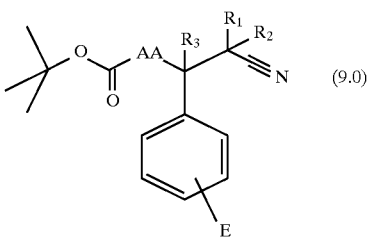

(9.0)

Compounds having formula (I) wherein: $R_a-K_1-W(=O)-$ is BOC (tert.-butyloxycarbonyl); Z is AA; G is a direct bond; Ar is phenyl; Q is a cyano group.

| COMP. Nr | AA | $R_1$ | $R_2$ | $R_3$ | E |
|---|---|---|---|---|---|
| 9.1 | [Val]—NH | H | H | H | — |
| 9.2 | [Val]—NH | H | H | H | 4-$OCH_3$ |
| 9.3 | [Val]—NH | H | H | H | 3,4-$OCH_3$ |
| 9.4 | [Val]—NH | H | H | H | 4-Cl |
| 9.5 | [Val]—NH | $CH_3$ | $CH_3$ | H | — |
| 9.6 | [Val]—NH | $CH_3$ | H | H | — |
| 9.7 | [Ile]—NH | $CH_3$ | H | H | — |
| 9.8 | [Val]—NH | $CH_3$ | $CH_3$ | H | 4-Cl |
| 9.9 | [Val]—NH | $CH_3$ | $CH_3$ | H | 4-$CF_3$ |

TABLE 10

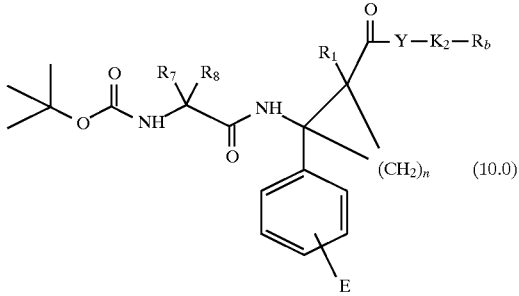

(10.0)

Compounds having formula (I) wherein: $R_a-K_1-W(=O)-$ is BOC (tert.-butyloxycarbonyl); Z is AA; G is a direct bond; Ar is phenyl; $R_2$ together with $R_3$ represents a $C_1-C_8$ alkylenic chain

| COMP. Nr | $R_1$ | $R_7$ | $R_8$ | Y | n | E | $K_2-R_b$ |
|---|---|---|---|---|---|---|---|
| 10.1 | H | H | $CH(CH_3)_2$ | O | 4 | — | $CH(CH_3)_2$ |

TABLE 11

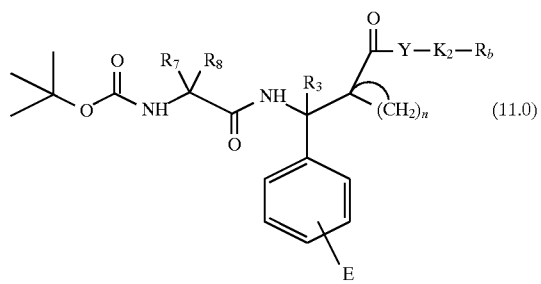

Compounds having formula (I) wherein: $R_a-K_1-W(=O)-$ is BOC (tert.-butyloxycarbonyl); Z is AA; G is a direct bond; Ar is phenyl; $R_2$ together with $R_1$ represents a $C_1-C_8$ alkylenic chain.

| COMP. Nr | $R_3$ | $R_7$ | $R_8$ | Y | n | E | $K_2-R_b$ |
|---|---|---|---|---|---|---|---|
| 11.1 | H | H | $CH(CH_3)_2$ | O | 4 | — | $CH(CH_3)_2$ |

TABLE 12

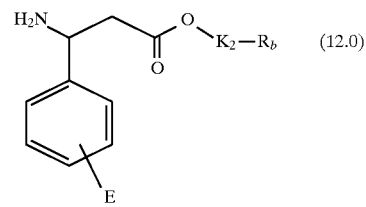

Compounds having formula (IX) wherein: $R_1$, $R_2$, $R_3$ and $R_5$ are hydrogen; Q is a group having general formula (III).

| COMPOUND NR. | E | $K_2-R_b$ |
|---|---|---|
| 12.1 | — | H |
| 12.2 | 4-$OCH_3$ | H |
| 12.3 | 4-Cl | H |
| 12.4 | 4-$CF_3$ | H |
| 12.5 | 4-CN | H |
| 12.6 | 4-Br | H |
| 12.7 | 4-Me | H |
| 12.8 | 4-Ethyl | H |

TABLE 13

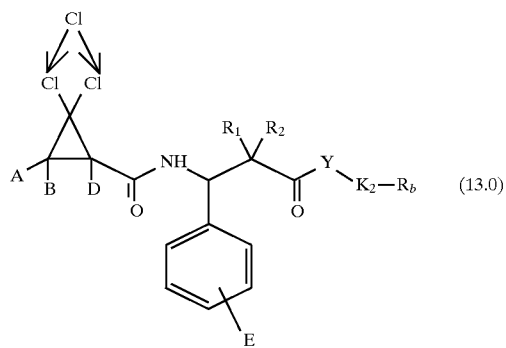

Compounds having formula (I) wherein: $R_1$, $R_2$, $R_3$ are hydrogen; $K_1$ is direct bond; $R_a$ is cyclopropane; W is a carbon atom;

| COMP. Nr | A | B | D | E | $Y-K_2-R_b$ | $R_1$ | $R_2$ |
|---|---|---|---|---|---|---|---|
| 13.1 | $CH_3$ | H | $CH_2CH_3$ | — | $O-CH_3$ | H | H |
| 13.2 | $CH_3$ | H | $CH_3$ | — | $O-CH(CH_3)_2$ | H | H |
| 13.3 | $CH_3$ | H | $CH(CH_3)_2$ | — | $O-CH_3$ | H | H |
| 13.4 | $CH_3$ | H | Cl | — | $O-CH_3$ | H | H |
| 13.5 | $CH_3$ | H | $CH_2CH_3$ | 4-Cl | $O-CH_3$ | H | H |
| 13.6 | $CH_3$ | H | $CH_3$ | 4-Cl | $O-CH_3$ | H | H |
| 13.7 | $CH_3$ | H | $CH_3$ | 4-$CF_3$ | $NH(CH_3)$ | H | H |
| 13.8 | $CH_3$ | H | $CH_3$ | — | $N(CH_3)_2$ | H | H |
| 13.9 | H | H | $CH_3$ | — | $O-CH(CH_3)_2$ | $CH_3$ | $CH_3$ |
| 13.10 | H | H | $CH_3$ | 4-Cl | $O-CH(CH_3)_2$ | $CH_3$ | $CH_3$ |
| 13.11 | $CH_3$ | H | $CH_3$ | — | $O-CH_3$ | $CH_3$ | $CH_3$ |
| 13.12 | $CH_2CH_3$ | H | $CH_3$ | — | $O-CH(CH_3)_2$ | H | H |

TABLE 14

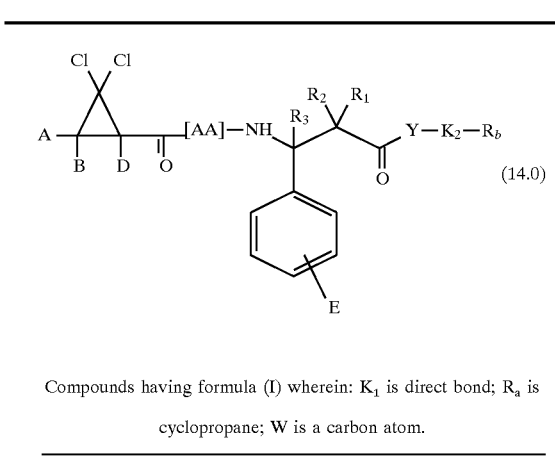

(14.0)

Compounds having formula (I) wherein: $K_1$ is direct bond; $R_a$ is cyclopropane; W is a carbon atom.

| COMP. Nr | A | B | D | AA | $R_3$ | $R_2$ | $R_1$ | $Y-K_2-R_b$ |
|---|---|---|---|---|---|---|---|---|
| 14.1 | H | H | $CH_3$ | [Gly] | H | H | H | $O-CH(CH_3)_2$ |
| 14.2 | H | H | $CH_3$ | β[Ala] | H | H | H | $O-CH(CH_3)_2$ |
| 14.3 | $CH_3$ | H | Ethyl | [Gly] | H | H | H | $O-CH_3$ |
| 14.4 | $CH_3$ | H | $CH_3$ | β[Ala] | H | H | H | $O-C(CH_3)_3$ |

TABLE 15

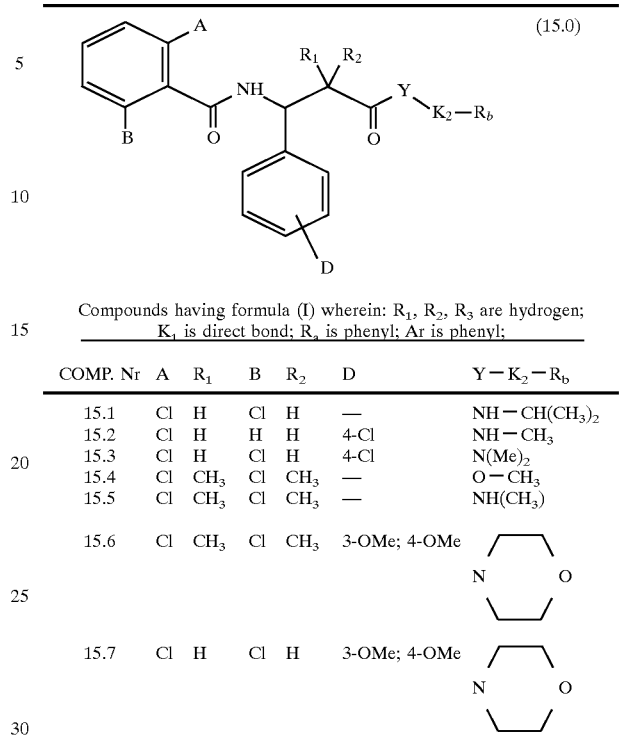

(15.0)

Compounds having formula (I) wherein: $R_1$, $R_2$, $R_3$ are hydrogen; $K_1$ is direct bond; $R_a$ is phenyl; Ar is phenyl;

| COMP. Nr | A | $R_1$ | B | $R_2$ | D | $Y-K_2-R_b$ |
|---|---|---|---|---|---|---|
| 15.1 | Cl | H | Cl | H | — | $NH-CH(CH_3)_2$ |
| 15.2 | Cl | H | H | H | 4-Cl | $NH-CH_3$ |
| 15.3 | Cl | H | Cl | H | 4-Cl | $N(Me)_2$ |
| 15.4 | Cl | $CH_3$ | Cl | $CH_3$ | — | $O-CH_3$ |
| 15.5 | Cl | $CH_3$ | Cl | $CH_3$ | — | $NH(CH_3)$ |
| 15.6 | Cl | $CH_3$ | Cl | $CH_3$ | 3-OMe; 4-OMe | morpholino |
| 15.7 | Cl | H | Cl | H | 3-OMe; 4-OMe | morpholino |

TABLE 16

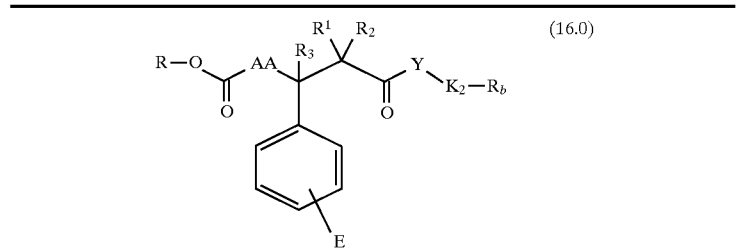

(16.0)

Compounds having formula (I) wherein: $R_a-K_1-W(=O)-$ is BOC (tert.-butyloxycarbonyl); Z is AA; Ar is phenyl;

| COMP. Nr. | $R_1$ | $R_2$ | $R_3$ | AA | R | $Y-K_2-R_b$ | E |
|---|---|---|---|---|---|---|---|
| 16.1 | H | H | H | [Val]—NH | $CH_2CH_3$ | $O-C(CH_3)_3$ | — |
| 16.2 | H | H | H | [Val]—NH | $CH(CH_3)_2$ | $O-C(CH_3)_3$ | — |
| 16.3 | H | H | H | [Val]—NH | Ph* | $O-C(CH_3)_3$ | — |
| 16.4 | H | H | H | [Val]—NH | $C(CH_3)_3$ | $NH-CH_3$ | — |
| 16.5 | H | H | H | [Val]—NH | $C(CH_3)_3$ | $NH-CH_3$ | 4-Cl |
| 16.6 | H | H | H | [Val]—NH | Ph | $O-CH_3$ | — |
| 16.7 | H | H | H | [Val]—NH | Ph | $O-CH_2CH_3$ | — |
| 16.8 | $CH_3$ | $CH_3$ | H | [Val]—NH | Ph | $O-CH_3$ | — |
| 16.9 | $CH_3$ | $CH_3$ | H | [Val]—NH | $CH(CH_3)_2$ | $O-CH_3$ | — |
| 16.10 | H | H | H | [Val]—NH | Ph | $NH-CH_3$ | — |
| 16.11 | H | H | H | [Val]—NH | Ph | $N(CH_3)_2$ | — |
| 16.12 | H | H | H | [Val]—NH | $CH(CH_3)_2$ | $NH-CH_3$ | — |
| 16.13 | H | H | H | [Val]—NH | $CH(CH_3)_2$ | $N(CH_3)_2$ | — |
| 16.14 | H | H | H | [Val]—NH | $C(CH_3)_3$ | $N(CH_3)_2$ | — |
| 16.15 | $CH_3$ | $CH_3$ | H | [Val]—NH | $C(CH_3)_3$ | $N(CH_3)_2$ | — |
| 16.16 | $CH_3$ | $CH_3$ | H | [Val]—NH | $CH(CH_3)_2$ | $N(CH_3)_2$ | — |
| 16.17 | $CH_3$ | $CH_3$ | H | [Val]—NH | Ph | $N(CH_3)_2$ | — |
| 16.18 | H | H | H | [Val]—NH | $CH(CH_3)_2$ | $NHCH(CH_3)_2$ | — |
| 16.19 | H | H | H | [Val]—NH | $CH(CH_3)_2$ | $NH-CH_2CH_3$ | — |

TABLE 16-continued

(16.0)

Compounds having formula (I) wherein: $R_a-K_1-W(=O)-$ is BOC (tert.-butyloxycarbonyl); Z is AA; Ar is phenyl;

| COMP. Nr. | $R_1$ | $R_2$ | $R_3$ | AA | R | $Y-K_2-R_b$ | E |
|---|---|---|---|---|---|---|---|
| 16.20 | H | H | H | [Val]—NH | $CH(CH_3)_2$ |  | — |
| 16.21 | H | H | H | [Val]—NH | $CH(CH_3)_2$ |  | — |
| 16.22 | H | H | H | [Leu]—NH | $CH(CH_3)_2$ | $N(Me)_2$ | — |
| 16.23 | $CH_3$ | $CH_3$ | H | [Val]—NH | $CH(CH_3)_2$ | $O-C_4H_9$ | — |
| 16.24 | $CH_3$ | $CH_3$ | H | [Val]—NH | $CH(CH_3)_2$ | $O-CH_2Ph$ | — |
| 16.25 | $CH_3$ | $CH_3$ | H | [Val]—NH | $CH(CH_3)_2$ | $O-C(CH_3)_2$ | — |
| 16.26 | H | H | H | [Val]—NH | Ph | $O-CH_2-CH_2$ | 4-CN |
| 16.27 | $CH_3$ | $CH_3$ | H | [Val]—NH | Ph | $O-CH_3$ | 4-F |
| 16.28 | H | H | H | [Val]—NH | Ph | $N(CH_3)_2$ | 4-Cl |
| 16.29 | H | H | H | [3AB]NH** | Ph | $O-CH(CH_3)_2$ | — |
| 16.30 | H | H | H | [CPA]NH*** | Ph | $O-CH_3$ | — |
| 16.31 | H | H | H | [Val]—NH | $CH(CH_3)_2$ | $N(CH_3)_2$ | 4-Cl |
| 16.32 | H | H | H | [Val]—NH | Ph | $N(CH_3)_2$ | 4CF_3 |
| 16.33 | $CH_3$ | $CH_3$ | H | [Val]—NH | $CH(CH_3)_2$ |  | 3OMe 4OMe |
| 16.34 | H | H | H | [Val]—NH | Ph |  | — |
| 16.35 | H | H | H | [3AB]NH | $CH(CH_3)_2$ | $N(Me)_2$ | 4-Cl |
| 16.36 | $CH_3$ | $CH_3$ | H | [3AB]NH | $CH(CH_3)_2$ | $O-CH_3$ | — |
| 16.37 | $CH_3$ | $CH_3$ | H | [3AC]NH**** | $CH(CH_3)_2$ | $O-CH_3$ | — |
| 16.38 | H | H | H | [Val]—NH | $CH(CH_3)_2$ |  | 4-Cl |
| 16.39 | H | H | H | [Val]—NH | $CH(CH_3)_2$ |  | 4-Cl |
| 16.40 | H | H | H | [Val]—NH | $CH(CH_3)_2$ |  | 4-Cl |

\* = Ph = Phenyl
\*\* = [3AB] = 3-aminobutanoyl
\*\*\* = [CPA] = cis-2-aminocyclopentylcarbonyl
\*\*\*\* = [3AC] = cis-2-amino-5-methyl-cycloesylcarbonyl

TABLE 17

(17.0)

Compounds having formula (I) wherein: $R_a-K_1-W(=O)-$ is BOC (tert.-butyloxycarbonyl); Z is AA; Ar is phenyl;

| COMP. Nr | $R_1$ | $R_2$ | $R_3$ | AA | Ar | $Y-K_1-R_b$ | R |
|---|---|---|---|---|---|---|---|
| 17.1 | H | H | H | [Val]—NH | thiophene (2-yl) | $OCH(CH_3)_2$ | $OCH(CH_3)_2$ |
| 17.2 | H | H | H | [Val]—NH | thiophene (2-yl) | $O-CH_3$ | Ph* |
| 17.3 | H | H | H | [Val]—NH | thiophene (2-yl) | $N(CH_3)_2$ | Ph |
| 17.4 | H | H | H | [Val]—NH | pyrimidine | $OCH(CH_3)_2$ | Ph |
| 17.5 | $CH_3$ | $CH_3$ | H | [Val]—NH | furan (2-yl) | $OCH(CH_3)_2$ | Ph |
| 17.6 | $CH_3$ | $CH_3$ | H | [Val]—NH | N-methylpyrrole | $N(Me)_2$ | Ph |
| 17.7 | $CH_3$ | $CH_3$ | H | [Val]—NH | N-methylimidazole | $N(Me)_2$ | Ph |

* = Ph = Phenyl

TABLE 18

(18.0)

Compounds having formula (I) wherein: $R_a-K_1-W(=O)-$ is BOC (tert.-butyloxycarbonyl); Z is AA; G is direct bond; Ar is phenyl; Q is a cyano group.

| COMP. Nr | AA | $R_1$ | $R_2$ | $R_3$ | E | R |
|---|---|---|---|---|---|---|
| 18.1 | [Val]—NH | $CH_3$ | $CH_3$ | H | — | $CH(CH_3)_2$ |
| 18.2 | [Val]—NH | $CH_3$ | $CH_3$ | H | 4-$OCH_3$ | $CH(CH_3)_2$ |
| 18.3 | [Val]—NH | $CH_3$ | H | H | — | Ph |
| 18.4 | [Val]—NH | H | H | $CH_3$ | — | Ph |
| 18.5 | [Val]—NH | H | H | H | 4-Cl | $CH(CH_3)_2$ |
| 18.6 | [Val]—NH | H | H | H | 4-$CF_3$ | $CH(CH_3)_2$ |
| 18.7 | [Val]—NH | $CH_3$ | $CH_3$ | H | 4-Cl | $CH(CH_3)_2$ |

TABLE 19

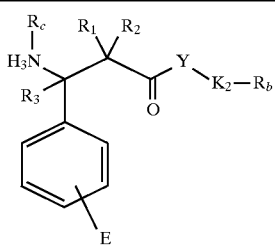

(19.0)

Compounds having formula (IX) wherein: Q is a group having general formula (III).

| COMP. Nr | $R_1$ | $R_2$ | $R_3$ | E | $Y-K_2-R_b$ | $R_c$ |
|---|---|---|---|---|---|---|
| 19.1 | H | H | H | — | $O-CH(CH_3)_2$ | PMP* |
| 19.2 | $CH_3$ | $CH_3$ | H | — | $O-CH(CH_3)_2$ | PMP |
| 19.3 | $CH_3$ | $CH_3$ | H | — | $O-CH_3$ | PMP |
| 19.4 | $CH_3$ | $CH_3$ | H | — | $O-CH_3$ | 4-ClPh** |
| 19.5 | $CH_3$ | $CH_3$ | H | — | $O-CH_3$ | Ph |
| 19.6 | $CH_3$ | $CH_3$ | H | — | $N(CH_3)_2$ | PMP |
| 19.7 | $CH_3$ | $CH_3$ | H | — | $NHCH_3$ | PMP |
| 19.8 | H | H | H | — | $N(CH_3)_2$ | PMP |
| 19.9 | $CH_3$ | $CH_3$ | H | 4-Cl | $O-CH(CH_3)_2$ | PMP |
| 19.10 | $CH_3$ | $CH_3$ | H | 4-$CH_3$ | $O-CH_3$ | PMP |
| 19.11 | $CH_3$ | $CH_3$ | H | 4-CN | $O-C(CH_3)_3$ | PMP |
| 19.12 | $CH_3$ | $CH_3$ | H | 4-Cl | $N(CH_3)_2$ | PMP |
| 19.13 | $CH_3$ | $CH_3$ | H | — | $O-CH_3$ | DMP*** |
| 19.14 | $CH_3$ | $CH_3$ | H | — | $O-CH_3$ | H |
| 19.15 | $CH_3$ | $CH_3$ | H | — | $O-CH(CH_3)_2$ | H |
| 19.16 | $CH_3$ | $CH_3$ | H | — | $O-C(CH_3)_3$ | H |
| 19.17 | $CH_3$ | $CH_3$ | $CF_3$ | — | $O-CH_3$ | PMP |
| 19.18 | $CH_3$ | $CH_3$ | $CF_3$ | — | $O-CH_3$ | H |
| 19.19 | $CH_3$ | H | H | — | $O-CH_3$ | H |
| 19.20 | $CH_3$ | H | H | — | $O-C(CH_3)_3$ | H |
| 19.21 | $CH_3$ | $CH_3$ | H | — | $N(CH_3)_2$ | H |
| 19.22 | H | H | H | — | $N(CH_3)_2$ | H |
| 19.23 | H | H | H | — | $NCH(CH_3)_2$ | H |
| 19.24 | H | H | H | — | $NH-CH_3$ | H |
| 19.25 | H | H | H | 4-Cl | $N(CH_3)_2$ | H |
| 19.26 | H | H | H | 4-Cl | $NH-CH_3$ | H |
| 19.27 | $CH_3$ | $CH_3$ | H | — | $NH-CH_3$ | H |

* = PMP = 4-methoxyphenyl
** = 4-ClPh = 4-chlorophenyl
*** = DMP = 4,6-dimethoxypyrimidin-2-yl

TABLE 20

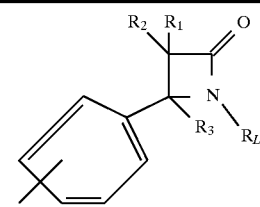

(20.0)

wherein $R_I$ is hydrogen

| COMPOUND Nr | $R_1$ | $R_2$ | $R_3$ | E |
|---|---|---|---|---|
| 20.1 | H | H | H | — |
| 20.2 | H | H | H | 4-OMe |
| 20.3 | H | $CH_3$ | H | — |
| 20.4 | $CH_3$ | $CH_3$ | H | — |
| 20.5 | $CH_3$ | $CH_3$ | H | 4-Cl |
| 20.6 | $CH_3$ | $CH_3$ | H | 4-CN |
| 20.7 | $CH_3$ | $CH_3$ | H | 4-$CH_3$ |
| 20.8 | $CH_3$ | $CH_3$ | H | 4-$CF_3$ |

TABLE 21

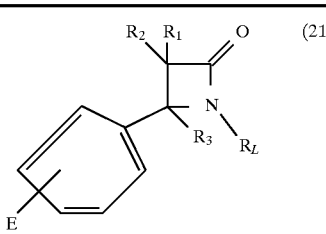

(21.0)

compounds of general formula (IXa)

| COMPOUND Nr | $R_1$ | $R_2$ | $R_3$ | E | $R_L$ |
|---|---|---|---|---|---|
| 21.1 | H | H | H | — | PMP[1] |
| 21.2 | $CH_3$ | $CH_3$ | H | — | PMP |
| 21.3 | $CH_3$ | H | H | — | PMP |
| 21.4 | $CH_3$ | $CH_3$ | H | — | 4-ClPh[2] |
| 21.5 | $CH_3$ | $CH_3$ | H | — | Ph |
| 21.6 | $CH_3$ | $CH_3$ | $CH_3$ | — | PMP |
| 21.7 | H | H | $CF_3$ | — | PMP |
| 21.8 | H | H | H | — | Ph |
| 21.9 | $CH_3$ | $CH_3$ | H | — | DMPYR[3] |
| 21.10 | $CH_3$ | $CH_3$ | H | — | PYR[4] |
| 21.11 | $CH_3$ | $CH_3$ | H | — | TZA[5] |
| 21.12 | $CH_3$ | $CH_3$ | H | — | TZB[6] |
| 21.13 | $CH_3$ | $CH_3$ | H | — | FEA[7] |

[1] = PMP = 4-methoxyphenyl
[2] = 4-ClPh = 4-chlorophenyl
[3] = DMPYR = 4,6-dimethoxypyrimidin-2-yl
[4] = PYR = pyrimidin-2-yl
[5] = TZA = thiazol-2-yl
[6] = TZB = 4,5 dimethylthiazole-2-yl
[7] = FEA = 1-phenylethyl (obtained according to BULL.SOC.CHEM.FR (1972) pag. 384)

TABLE 22

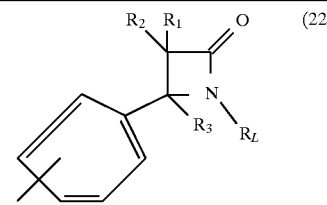

(22.0)

Compounds of general formula (IXa) obtained from the products listed in Table 20, by using the acylation procedure shown in TELE (Tetrahedron Letters) 1990 Vol. 31 pag. 6429.

| COMPOUND Nr | $R_1$ | $R_2$ | $R_3$ | E | $R_L$ |
|---|---|---|---|---|---|
| 22.1 | H | H | H | — | $CO-Ph$* |
| 22.2 | H | H | H | 4-OMe | $CO-Ph$ |
| 22.3 | H | $CH_3$ | H | — | $COCH_2Ph$ |
| 22.4 | $CH_3$ | $CH_3$ | H | — | $CO-O-CH(CH_3)_2$ |
| 22.5 | $CH_3$ | $CH_3$ | H | — | $CO-Ph$ |
| 22.6 | $CH_3$ | $CH_3$ | H | 4-Cl | $CO-Ph$ |
| 22.7 | $CH_3$ | $CH_3$ | H | 4-$CH_3$ | $CO-Ph$ |
| 22.8 | $CH_3$ | $CH_3$ | H | 4-CH | $CO-Ph$ |
| 22.9 | $CH_3$ | $CH_3$ | H | — | 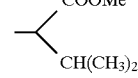 |

TABLE 22-continued

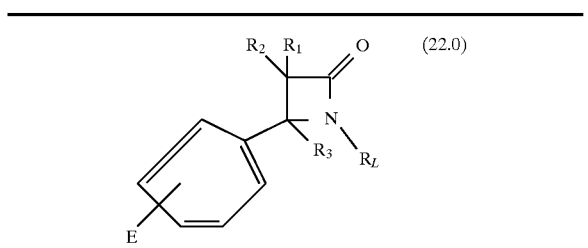

Compounds of general formula (IXa) obtained from the products listed in Table 20, by using the acylation procedure shown in TELE (Tetrahedron Letters) 1990 Vol. 31 pag. 6429.

| COMPOUND Nr | $R_1$ | $R_2$ | $R_3$ | E | $R_L$ |
|---|---|---|---|---|---|
| 22.10 | $CH_3$ | $CH_3$ | H | — | COOCH(Me)$_2$, CH(CH$_3$)$_2$ |
| 22.11 | H | H | H | — | COOMe, CH$_2$-Ph |
| 22.12 | H | H | H | — | COOC(CH$_3$)$_3$, CH$_2$-Ph |

* = Ph = Phenyl

TABLE 23

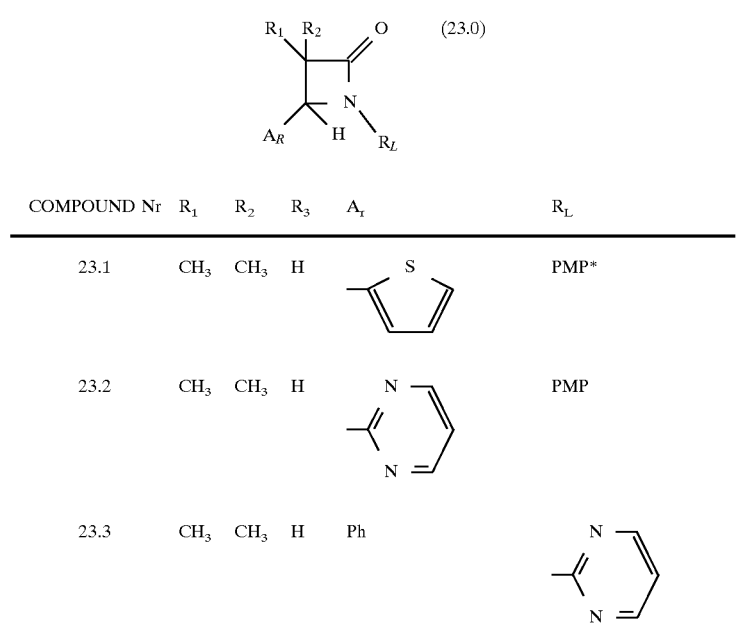

| COMPOUND Nr | $R_1$ | $R_2$ | $R_3$ | $A_r$ | $R_L$ |
|---|---|---|---|---|---|
| 23.1 | $CH_3$ | $CH_3$ | H | 2-thienyl | PMP* |
| 23.2 | $CH_3$ | $CH_3$ | H | 2-pyrimidinyl | PMP |
| 23.3 | $CH_3$ | $CH_3$ | H | Ph | 2-pyrimidinyl |

TABLE 23-continued

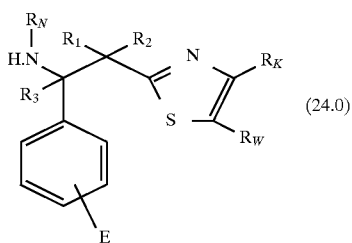

(23.0)

| COMPOUND Nr | R₁ | R₂ | R₃ | Aᵣ | R_L |
|---|---|---|---|---|---|
| 23.4 | CH₃ | CH₃ | H | Ph | (thiazoline-S,N) |
| 23.5 | CH₃ | CH₃ | H | Ph | (pyridine-CF₃) |
| 23.6 | CH₃ | CH₃ | H | Ph | (pyrimidine-diOCH₃) |
| 23.7 | CH₃ | CH₃ | H | (benzofuran) | PMP |

\* = PMP = 4-methoxyphenyl

TABLE 24

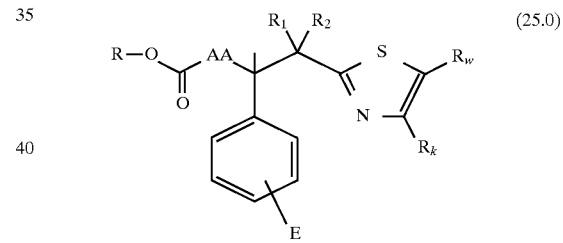

(24.0)

compound of general formula (IX) wherein Q is thiazole and $R_3$ is hydrogen

| COMPOUND Nr | R₁ | R₂ | E | R_W | R_k | R_N |
|---|---|---|---|---|---|---|
| 24.1 | H | H | H | CH₃ | CH₃ | H |
| 24.2 | H | CH₃ | H | CH₃ | CH₃ | H |
| 24.3 | H | H | 4-Cl | CH₃ | CH₃ | H |
| 24.4 | H | H | H | H | H | H |
| 24.5 | H | H | 4-Cl | H | H | H |
| 24.6 | CH₃ | H | H | H | H | PMP* |
| 24.7 | H | H | H | CH₃ | CH₃ | FEA** |
| 24.8[1] | CH₃ | CH₃ | H | CH₃ | CH₃ | H |
| 24.9[1] | CH₃ | CH₃ | 4-F | CH₃ | CH₃ | H |

[1] obtained following the method described in "Tetrahedron Letters" 1986 Vol. 27 pag. 3033
\*PMP = 4-methoxyphenyl
\*\*FEA = 1-phenylethyl

TABLE 25

(25.0)

compounds having general formula (I) wherein $R_3$ is hydrogen; Z is AA; Ar is phenyl; Q is substituted thiazole.

| COMP. Nr | R₁ | R₂ | R | AA | R_k | R_w | E |
|---|---|---|---|---|---|---|---|
| 25.1 | H | H | C(CH₃)₃ | [Val]—NH | CH₃ | CH₃ | H |
| 25.2 | H | H | CH(CH₃)₂ | [Val]—NH | CH₃ | CH₃ | H |
| 25.3 | H | H | Ph* | [Val]—NH | CH₃ | CH₃ | H |
| 25.4 | H | H | Ph | [Val]—NH | H | H | H |
| 25.5 | H | H | CH(CH₃)₂ | [Val]—NH | H | H | 4-Cl |
| 25.6 | H | H | C(CH₃)₃ | [Leu]—NH | CH₃ | CH₃ | 4-Br |

\* = Ph = Phenyl

TABLE 26

(26.0)

compounds having general formula (IX) wherein $R_1$, $R_2$, $R_3$ and $R_c$ are hydrogen; Q is a group having general formula (III).

| COMPOUND NR. | E | $K_2-R_b$ |
|---|---|---|
| 26.1 | 4-Cl | $CH_3$ |
| 26.2 | — | $CH_3$ |
| 26.3 | 4-Cl | $CH_2CH_3$ |
| 26.4 | — | $CH_2CH_3$ |
| 26.5 | 4-$SO_2CH_3$ | $CH_3$ |
| 26.6 | 3-$COOCH(CH_3)_2$ | $CH_3$ |
| 26.7 | 3-$COOCH_3$ | $CH_3$ |
| 26.8 | — | $C(CH_3)_3$ |
| 26.9 | — | $CH(CH_3)_2$ |
| 26.10 | 4-$OCH_3$ | $CH_2Ph$* |
| 26.11 | — | $CH_2Ph$ |

* = Ph = Phenyl

TABLE 27

(27.0)

compounds having general formula (IX) whrerein and Q is a group having general formula (III) and $Y-K_2-R_b$ is hydroxyl group

| COMPOUND Nr | $R_1$ | $R_2$ | $R_3$ | E | $R_c$ |
|---|---|---|---|---|---|
| 27.1 | $CH_3$ | $CH_3$ | H | — | PMP* |
| 27.2 | $CH_3$ | $CH_3$ | H | 4-CN | PMP |
| 27.3 | $CH_3$ | H | H | — | H |
| 27.4 | $CH_3$ | $CH_3$ | H | 4-Cl | H |
| 27.5 | $CH_3$ | $CH_3$ | H | 4-Cl | PMP |
| 27.6 | $CH_3$ | $CH_3$ | H | — | H |

* = PMP = 4-methoxyphenyl

TABLE 28

(28.0)

compound of general formula (IX) wherein $R_3$ is hydrogen

| COMPOUND Nr. | $R_1$ | $R_2$ | Ar | $R_c$ | Q |
|---|---|---|---|---|---|
| 28.1 | $CH_3$ | $CH_3$ | thienyl (S) | PMP* | $CO-O-CH_3$ |

TABLE 28-continued (28.0)

compound of general formula (IX) wherein $R_3$ is hydrogen

| COMPOUND Nr. | $R_1$ | $R_2$ | Ar | $R_c$ | Q |
|---|---|---|---|---|---|
| 28.2 | H | H | thienyl (S) | H | COOH |
| 28.3 | $CH_3$ | $CH_3$ | furyl (O) | PMP | $CO-O-CH_3$ |
| 28.4 | $CH_3$ | $CH_3$ | thienyl (S) | PMP | $CONH-CH_3$ |
| 28.5 | $CH_3$ | $CH_3$ | Ph** | PMP | CN |
| 28.6 | $CH_3$ | $CH_3$ | Ph | H | CN |

* = PMP = 4-methoxyphenyl
** = Ph = phenyl

TABLE 29

(29.0)

compounds having general formula (I) wherein $K_1$ is a group NRZ

| COMP. Nr | $R_a$ | $R_z$ | $R_1$ | $R_2$ | E | Q |
|---|---|---|---|---|---|---|
| 29.1 | $CH_3$ | $CH_3$ | H | H | 4-Cl | $COOCH(CH_3)_2$ |
| 29.2 | $CH_3$ | $CH_3$ | H | H | 4-Cl | $COOC(CH_3)_3$ |
| 29.3 | H | $CH_3$ | H | H | — | $COOC(CH_3)_3$ |
| 29.4 | H | $HC(CH_3)_2$ | H | H | 4-Cl | $COOC(CH_3)_3$ |
| 29.5 | $CH_3$ | $CH_3$ | H | H | 4-Cl | CN |
| 29.6 | $CH_3$ | $CH_3$ | $CH_3$ | $CH_3$ | 4-Cl | $CON(CH_3)_2$ |

TABLE 30

Elemental analysis of the synthesized compounds

| COMPOUND Nr | THEORETICAL % | FOUND % |
|---|---|---|
| 1.1 | C: 56.99 | C: 57.04 |
|  | H: 5.91 | H: 5.88 |
|  | N: 3.91 | N: 3.96 |
| 1.2 | C: 62.08 | C: 62.12 |
|  | H: 5.21 | H: 5.20 |
|  | N: 3.45 | N: 3.48 |
| 1.3 | C: 55.68 | C: 55.68 |
|  | H: 5.97 | H: 5.94 |
|  | N: 3.61 | N: 3.66 |
| 1.4 | C: 51.99 | C: 51.87 |
|  | H: 5.13 | H: 5.10 |
|  | N: 3.57 | N: 3.60 |
| 1.5 | C: 53.74 | C: 53.78 |
|  | H: 5.26 | H: 5.21 |

TABLE 30-continued

Elemental analysis of the synthesized compounds

| COMPOUND Nr | THEORETICAL % | FOUND % |
|---|---|---|
| 1.6 | N: 3.48<br>C: 59.07<br>H: 6.52 | N: 3.44<br>C: 59.10<br>H: 6.55 |
| 1.7 | N: 3.63<br>C: 69.79<br>H: 7.69 | N: 3.70<br>C: 69.83<br>H: 7.68 |
| 1.8 | N: 5.09<br>C: 75.19<br>H: 7.17 | N: 5.08<br>C: 75.21<br>H: 7.17 |
| 1.9 | N: 3.99<br>C: 54.56<br>H: 5.19 | N: 3.98<br>C: 54.54<br>H: 5.21 |
| 1.10 | N: 4.24<br>C: 51.99<br>H: 5.13 | N: 4.24<br>C: 52.03<br>H: 5.15 |
| 1.11 | N: 3.57<br>C: 51.74<br>H: 4.63 | N: 3.61<br>C: 51.76<br>H: 4.65 |
| 2.1 | N: 4.02<br>C: 60.01<br>H: 5.04 | N: 4.08<br>C: 60.05<br>H: 5.10 |
| 2.2 | N: 3.68<br>C: 65.99<br>H: 5.83 | N: 3.62<br>C: 65.96<br>H: 5.81 |
| 2.3 | N: 4.05<br>C: 53.59<br>H: 4.05 | N: 4.11<br>C: 53.62<br>H: 4.02 |
| 3.1 | N: 3.12<br>C: 66.43<br>H: 8.20 | N: 3.16<br>C: 66.43<br>H: 8.21 |
| 3.2 | N: 4.56<br>C: 67.26<br>H: 8.47 | N: 4.54<br>C: 67.28<br>H: 8.44 |
| 3.3 | N: 4.36<br>C: 66.64<br>H: 8.55 | N: 4.39<br>C: 66.59<br>H: 8.58 |
| 3.4 | N: 9.14<br>C: 65.00<br>H: 8.43 | N: 9.17<br>C: 65.02<br>H: 8.41 |
| 3.5 | N: 6.89<br>C: 67.26<br>H: 8.47 | N: 6.86<br>C: 67.24<br>H: 8.47 |
| 3.6 | N: 4.36<br>C: 68.03<br>H: 8.71 | N: 4.34<br>C: 68.05<br>H: 8.69 |
| 3.7 | N: 4.18<br>C: 68.23<br>H: 9.04 | N: 4.17<br>C: 68.24<br>H: 9.03 |
| 4.1 | N: 8.38<br>C: 65.69<br>H: 8.63 | N: 8.40<br>C: 65.01<br>H: 8.70 |
| 4.2 | N: 6.66<br>C: 66.33<br>H: 8.81 | N: 6.50<br>C: 66.92<br>H: 8.85 |
| 4.3 | N: 6.45<br>C: 66.33<br>H: 8.81 | N: 6.32<br>C: 66.20<br>H: 8.84 |
| 4.4 | N: 6.45<br>C: 63.47<br>H: 7.99 | N: 6.38<br>C: 63.48<br>H: 7.99 |
| 4.5 | N: 7.40<br>C: 64.26<br>H: 8.22 | N: 7.39<br>C: 64.27<br>H: 8.23 |
| 4.6 | N: 7.14<br>C: 65.00<br>H: 8.43 | N: 7.15<br>C: 65.01<br>H: 8.44 |
| 4.7 | N: 6.89<br>C: 65.69<br>H: 8.63 | N: 6.84<br>C: 65.67<br>H: 8.64 |
| 4.8 | N: 6.66<br>C: 65.69<br>H: 8.63 | N: 6.64<br>C: 65.70<br>H: 8.63 |
| 4.9 | N: 6.66<br>C: 65.69<br>H: 8.63 | N: 6.67<br>C: 65.73<br>H: 8.60 |

TABLE 30-continued

Elemental analysis of the synthesized compounds

| COMPOUND Nr | THEORETICAL % | FOUND % |
|---|---|---|
| 4.10 | N: 6.66<br>C: 58.18<br>H: 7.08 | N: 6.68<br>C: 58.16<br>H: 7.10 |
| 4.11 | N: 0.78<br>C: 64.26<br>H: 8.22 | N: 6.78<br>C: 64.25<br>H: 8.21 |
| 4.12 | N: 7.14<br>C: 65.00<br>H: 8.43 | N: 7.12<br>C: 65.03<br>H: 8.45 |
| 4.13 | N: 6.89<br>C: 62.54<br>H: 8.11 | N: 6.90<br>C: 62.54<br>H: 8.11 |
| 4.14 | N: 6.63<br>C: 64.02<br>H: 7.71 | N: 6.63<br>C: 64.03<br>H: 7.70 |
| 4.15 | N: 9.74<br>C: 63.29<br>H: 7.48 | N: 9.73<br>C: 63.30<br>H: 7.48 |
| 4.16 | N: 10.06<br>C: 64.02<br>H: 7.71 | N: 10.07<br>C: 64.01<br>H: 7.70 |
| 4.17 | N: 9.74<br>C: 62.25<br>H: 7.84 | N: 9.72<br>C: 62.23<br>H: 7.83 |
| 4.18 | N: 6.60<br>C: 59.92<br>H: 7.54 | N: 6.60<br>C: 59.95<br>H: 7.54 |
| 4.19 | N: 6.35<br>C: 65.69<br>H: 8.63 | N: 6.34<br>C: 65.70<br>H: 8.63 |
| 4.20 | N: 6.66<br>C: 66.33<br>H: 8.81 | N: 6.65<br>C: 66.33<br>H: 8.80 |
| 4.21 | N: 6.45<br>C: 58.22<br>H: 7.01 | N: 6.42<br>C: 58.21<br>H: 7.00 |
| 4.22 | N: 5.90<br>C: 63.47<br>H: 7.99 | N: 5.89<br>C: 63.49<br>H: 8.00 |
| 4.23 | N: 7.40<br>C: 55.17<br>H: 6.56 | N: 7.38<br>C: 55.16<br>H: 6.55 |
| 4.24 | N: 5.36<br>C: 64.63<br>H: 8.68 | N: 5.35<br>C: 64.65<br>H: 8.68 |
| 4.25 | N: 6.03<br>C: 67.95<br>H: 7.86 | N: 6.02<br>C: 67.98<br>H: 7.87 |
| 4.26 | N: 5.46<br>C: 66.10<br>H: 8.63 | N: 5.46<br>C: 66.11<br>H: 8.63 |
| 4.27 | N: 5.71<br>C: 66.01<br>H: 8.19 | N: 5.72<br>C: 66.02<br>H: 8.20 |
| 4.28 | N: 6.69<br>C: 64.26<br>H: 8.22 | N: 6.69<br>C: 64.25<br>H: 8.21 |
| 4.29 | N: 7.14<br>C: 61.78<br>H: 8.21 | N: 7.15<br>C: 61.77<br>H: 8.20 |
| 4.30 | N: 6.00<br>C: 58.65<br>H: 7.49 | N: 6.02<br>C: 58.63<br>H: 7.48 |
| 4.31 | N: 5.95<br>C: 59.92<br>H: 7.54 | N: 5.96<br>C: 59.92<br>H: 7.54 |
| 4.32 | N: 6.35<br>C: 56.50<br>H: 6.55 | N: 6.34<br>C: 56.51<br>H: 6.56 |
| 5.1 | N: 6.27<br>C: 64.60<br>H: 7.74 | N: 6.28<br>C: 64.56<br>H: 7.78 |
| 5.2 | N: 7.17<br>C: 62.84<br>H: 7.67 | N: 7.21<br>C: 62.92<br>H: 7.71 |

TABLE 30-continued

Elemental analysis of the synthesized compounds

| COMPOUND Nr | THEORETICAL % | FOUND % |
|---|---|---|
| 6.1 | N: 6.66<br>C: 66.01<br>H: 8.19 | N: 6.66<br>C: 66.02<br>H: 8.17 |
| 6.2 | N: 6.69<br>C: 66.64<br>H: 8.39 | N: 6.73<br>C: 66.68<br>H: 8.43 |
| 6.3 | N: 6.48<br>C: 65.32<br>H: 7.97 | N: 6.51<br>C: 65.36<br>H: 8.00 |
| 7.1 | N: 6.93<br>C: 66.64<br>H: 8.39 | N: 6.89<br>C: 66.61<br>H: 8.36 |
| 7.2 | N: 6.48<br>C: 67.24<br>H: 8.58 | N: 6.46<br>C: 67.32<br>H: 8.61 |
| 8.1 | N: 6.27<br>C: 66.01<br>H: 8.19 | N: 6.25<br>C: 66.03<br>H: 8.15 |
| 8.2 | N: 6.69<br>C: 66.64<br>H: 8.39 | N: 6.63<br>C: 66.61<br>H: 8.41 |
| 9.1 | N: 6.48<br>C: 66.06<br>H: 7.88<br>N: 12.16 | N: 6.46<br>C: 66.06<br>H: 7.90<br>N: 12.20 |
| 9.2 | C: 63.98<br>H: 7.79<br>N: 11.19 | C: 64.00<br>H: 7.78<br>N: 11.17 |
| 9.3 | C: 62.20<br>H: 7.71<br>N: 10.36 | C: 62.18<br>H: 7.75<br>N: 10.40 |
| 9.4 | C: 60.07<br>H: 6.90<br>N: 11.06 | C: 59.98<br>H: 6.91<br>N: 11.10 |
| 9.5 | C: 67.53<br>H: 8.37<br>N: 11.25 | C: 67.52<br>H: 8.35<br>N: 11.25 |
| 9.6 | C: 66.83<br>H: 8.13<br>N: 11.69 | C: 66.80<br>H: 8.13<br>N: 11.68 |
| 9.7 | C: 67.53<br>H: 8.37<br>N: 11.25 | C: 67.54<br>H: 8.36<br>N: 11.25 |
| 9.8 | C: 61.83<br>H: 7.41<br>N: 10.30 | C: 61.83<br>H: 7.41<br>N: 10.28 |
| 9.9 | C: 59.85<br>H: 6.85<br>N: 9.52 | C: 59.84<br>H: 6.84<br>N: 9.54 |
| 10.1 | C: 67.80<br>H: 8.75<br>N: 6.08 | C: 67.78<br>H: 8.73<br>N: 6.06 |
| 11.1 | C: 67.80<br>H: 8.75<br>N: 6.08 | C: 67.82<br>H: 8.75<br>N: 6.11 |
| 12.1 | C: 65.44<br>H: 6.71<br>N: 8.48 | C: 65.50<br>H: 6.71<br>N: 8.47 |
| 12.2 | C: 61.53<br>H: 6.71<br>N: 7.17 | C: 61.58<br>H: 6.69<br>N: 7.17 |
| 12.3 | C: 54.15<br>H: 5.05<br>N: 7.02 | C: 54.09<br>H: 5.09<br>N: 7.04 |
| 12.4 | C: 51.51<br>H: 4.32<br>N: 6.01 | C: 51.55<br>H: 4.33<br>N: 6.08 |
| 12.5 | C: 63.15<br>H: 5.30<br>N: 14.73 | C: 63.11<br>H: 5.32<br>N: 14.70 |
| 12.6 | C: 44.29<br>H: 4.13<br>N: 5.74 | C: 44.31<br>H: 4.15<br>N: 5.76 |
| 12.7 | C: 67.02<br>H: 7.31 | C: 66.99<br>H: 7.34 |
| 12.8 | N: 7.83<br>C: 68.37<br>H: 7.82 | N: 7.85<br>C: 68.37<br>H: 7.84 |
| 13.1 | N: 7.25<br>C: 56.99<br>H: 5.91<br>N: 3.91 | N: 7.27<br>C: 57.00<br>H: 5.90<br>N: 3.93 |
| 13.2 | C: 58.07<br>H: 6.23<br>N: 3.76 | C: 58.10<br>H: 6.21<br>N: 3.72 |
| 13.3 | C: 58.07<br>H: 6.23<br>N: 3.76 | C: 58.07<br>H: 6.24<br>N: 3.79 |
| 13.4 | C: 49.41<br>H: 4.42<br>N: 3.84 | C: 49.39<br>H: 4.41<br>N: 3.81 |
| 13.5 | C: 51.99<br>H: 5.13<br>N: 3.57 | C: 52.01<br>H: 5.11<br>N: 3.58 |
| 13.6 | C: 50.75<br>H: 4.79<br>N: 3.70 | C: 50.73<br>H: 4.80<br>N: 3.72 |
| 13.7 | C: 49.65<br>H: 4.66<br>N: 6.81 | C: 49.66<br>H: 4.64<br>N: 6.85 |
| 13.8 | C: 57.15<br>H: 6.21<br>N: 7.84 | C: 57.17<br>H: 6.23<br>N: 7.86 |
| 13.9 | C: 59.07<br>H: 6.52<br>N: 3.63 | C: 59.07<br>H: 6.54<br>N: 3.63 |
| 13.10 | C: 54.24<br>H: 5.75<br>N: 3.33 | C: 54.26<br>H: 5.77<br>N: 3.31 |
| 13.11 | C: 58.07<br>H: 6.23<br>N: 3.76 | C: 58.10<br>H: 6.26<br>N: 3.72 |
| 13.12 | C: 59.07<br>H: 6.52<br>N: 3.63 | C: 59.06<br>H: 6.53<br>N: 3.61 |
| 14.1 | C: 54.95<br>H: 5.82<br>N: 6.75 | C: 54.94<br>H: 5.84<br>N: 6.76 |
| 14.2 | C: 55.95<br>H: 6.10<br>N: 6.52 | C: 55.97<br>H: 6.12<br>N: 6.53 |
| 14.3 | C: 54.95<br>H: 5.82<br>N: 6.75 | C: 54.92<br>H: 5.80<br>N: 6.75 |
| 14.4 | C: 56.89<br>H: 6.37<br>N: 6.32 | C: 56.90<br>H: 6.39<br>N: 6.30 |
| 15.1 | C: 60.17<br>H: 5.32<br>N: 7.39 | C: 60.20<br>H: 5.32<br>N: 7.38 |
| 15.2 | C: 52.94<br>H: 3.92<br>N: 7.26 | C: 52.93<br>H: 3.91<br>N: 7.28 |
| 15.3 | C: 54.09<br>H: 4.29<br>N: 7.01 | C: 54.10<br>H: 4.31<br>N: 7.03 |
| 15.4 | C: 60.01<br>H: 5.04<br>N: 3.68 | C: 60.04<br>H: 5.03<br>N: 3.69 |
| 15.5 | C: 60.17<br>H: 5.32<br>N: 7.39 | C: 60.19<br>H: 5.34<br>N: 7.40 |
| 15.6 | C: 58.19<br>H: 5.70<br>N: 5.65 | C: 58.17<br>H: 5.69<br>N: 5.64 |
| 15.7 | C: 56.54<br>H: 5.18<br>N: 5.99 | C: 56.55<br>H: 5.17<br>N: 6.00 |
| 16.1 | C: 64.26<br>H: 8.22 | C: 64.23<br>H: 8.20 |

TABLE 30-continued

Elemental analysis of the synthesized compounds

| COMPOUND Nr | THEORETICAL % | FOUND % |
|---|---|---|
|  | N: 7.14 | N: 7.16 |
| 16.2 | C: 65.00 | C: 64.99 |
|  | H: 8.43 | H: 8.42 |
|  | N: 6.89 | N: 6.90 |
| 16.3 | C: 68.16 | C: 68.18 |
|  | H: 7.32 | H: 7.34 |
|  | N: 6.36 | N: 6.35 |
| 16.4 | C: 63.64 | C: 63.65 |
|  | H: 8.28 | H: 8.28 |
|  | N: 11.13 | N: 11.15 |
| 16.5 | C: 58.32 | C: 58.37 |
|  | H: 7.34 | H: 7.33 |
|  | N: 10.20 | N: 10.21 |
| 16.6 | C: 66.32 | C: 66.35 |
|  | H: 6.58 | H: 5.60 |
|  | N: 7.03 | N: 7.02 |
| 16.7 | C: 66.97 | C: 66.96 |
|  | H: 6.84 | H: 6.85 |
|  | N: 6.79 | N: 6.80 |
| 16.8 | C: 67.59 | C: 67.61 |
|  | H: 7.09 | H: 7.09 |
|  | N: 6.57 | N: 6.55 |
| 16.9 | C: 64.26 | C: 64.28 |
|  | H: 8.22 | H: 8.24 |
|  | N: 7.14 | N: 7.15 |
| 16.10 | C: 66.48 | C: 66.50 |
|  | H: 6.85 | H: 6.86 |
|  | N: 10.57 | N: 10.56 |
| 16.11 | C: 67.13 | C: 67.10 |
|  | H: 7.10 | H: 7.12 |
|  | N: 10.21 | N: 10.19 |
| 16.12 | C: 62.79 | C: 62.79 |
|  | H: 8.04 | H: 8.04 |
|  | N: 11.56 | N: 11.58 |
| 16.13 | C: 63.64 | C: 63.65 |
|  | H: 8.28 | H: 8.29 |
| 16.14 | C: 64.43 | C: 64.40 |
|  | H: 8.50 | H: 8.49 |
|  | N: 10.73 | N: 10.71 |
| 16.15 | C: 65.84 | C: 65.82 |
|  | H: 8.89 | H: 8.91 |
|  | N: 10.02 | N: 9.99 |
| 16.16 | C: 65.16 | C: 65.17 |
|  | H: 8.70 | H: 8.72 |
|  | N: 10.36 | N: 10.36 |
| 16.17 | C: 68.31 | C: 68.29 |
|  | H: 7.57 | H: 7.58 |
|  | N: 9.56 | N: 9.55 |
| 16.18 | C: 64.43 | C: 64.41 |
|  | H: 8.50 | H: 8.51 |
|  | N: 10.73 | N: 10.71 |
| 16.19 | C: 63.64 | C: 63.65 |
|  | H: 8.28 | H: 8.30 |
|  | N: 11.13 | N: 11.15 |
| 16.20 | C: 65.48 | C: 65.48 |
|  | H: 8.24 | H: 8.23 |
|  | N: 10.41 | N: 10.40 |
| 16.21 | C: 62.99 | C: 63.00 |
|  | H: 7.93 | H: 7.91 |
|  | N: 10.02 | N: 10.00 |
| 16.22 | C: 64.43 | C: 64.45 |
|  | H: 8.50 | H: 8.51 |
|  | N: 10.73 | N: 10.74 |
| 16.23 | C: 66.33 | C: 66.35 |
|  | H: 8.81 | H: 8.82 |
|  | N: 6.45 | N: 6.45 |
| 16.24 | C: 69.21 | C: 69.19 |
|  | H: 7.74 | H: 7.74 |
|  | N: 5.98 | N: 5.60 |
| 16.25 | C: 66.33 | C: 66.31 |
|  | H: 8.79 | H: 8.80 |
|  | N: 6.45 | N: 6.44 |
| 16.26 | C: 65.89 | C: 65.90 |
|  | H: 6.22 | H: 6.20 |
|  | N: 9.60 | N: 9.59 |
| 16.27 | C: 64.85 | C: 64.85 |
|  | H: 6.58 | H: 6.57 |
|  | N: 6.30 | N: 6.28 |
| 16.28 | C: 61.95 | C: 61.97 |
|  | H: 6.33 | H: 6.34 |
|  | N: 9.42 | N: 9.41 |
| 16.29 | C: 66.97 | C: 66.98 |
|  | H: 6.84 | H: 6.84 |
|  | N: 6.79 | N: 6.81 |
| 16.30 | C: 67.30 | C: 67.29 |
|  | H: 6.38 | H: 6.40 |
|  | N: 6.82 | N: 6.81 |
| 16.31 | C: 58.32 | C: 58.35 |
|  | H: 7.34 | H: 7.36 |
|  | N: 10.20 | N: 10.22 |
| 16.32 | C: 60.12 | C: 60.15 |
|  | H: 5.89 | H: 5.90 |
|  | N: 8.76 | N: 8.78 |
| 16.33 | C: 61.52 | C: 61.50 |
|  | H: 8.14 | H: 8.12 |
|  | N: 8.28 | N: 8.31 |
| 16.34 | C: 66.21 | C: 66.19 |
|  | H: 6.89 | H: 6.90 |
|  | N: 9.26 | N: 9.24 |
| 16.35 | C: 57.35 | C: 57.37 |
|  | H: 7.09 | H: 7.11 |
|  | N: 10.56 | N: 10.55 |
| 16.36 | C: 63.47 | C: 63.49 |
|  | H: 7.99 | H: 7.99 |
|  | N: 7.40 | N: 7.39 |
| 16.37 | C: 66.64 | C: 66.63 |
|  | H: 8.39 | H: 8.37 |
|  | N: 6.48 | N: 6.50 |
| 16.38 | C: 59.50 | C: 59.53 |
|  | H: 7.13 | H: 7.14 |
|  | N: 9.91 | N: 9.91 |
| 16.39 | C: 59.50 | C: 59.48 |
|  | H: 7.13 | H: 7.15 |
|  | N: 9.91 | N: 9.95 |
| 16.40 | C: 60.33 | C: 60.30 |
|  | H: 7.36 | H: 7.34 |
|  | N: 9.59 | N: 9.55 |
| 17.1 | C: 57.26 | C: 57.23 |
|  | H: 7.59 | H: 7.57 |
|  | N: 7.03 | N: 7.06 |
| 17.2 | C: 59.39 | C: 59.39 |
|  | H: 5.98 | H: 5.92 |
|  | N: 6.93 | N: 6.93 |
| 17.3 | C: 60.41 | C: 60.44 |
|  | H: 6.52 | H: 6.50 |
|  | N: 10.06 | N: 10.03 |
| 17.4 | C: 61.67 | C: 61.68 |
|  | H: 6.59 | H: 6.57 |
|  | N: 13.08 | N: 13.09 |
| 17.5 | C: 64.85 | C: 64.87 |
|  | H: 7.26 | H: 7.27 |
|  | N: 6.30 | N: 6.32 |
| 17.6 | C: 65.14 | C: 65.12 |
|  | H: 7.74 | H: 7.75 |
|  | N: 12.66 | N: 12.68 |
| 17.7 | C: 62.28 | C: 62.27 |
|  | H: 7.50 | H: 7.52 |
|  | N: 15.79 | N: 15.78 |
| 18.1 | C: 66.83 | C: 66.81 |
|  | H: 8.13 | H: 8.14 |
|  | N: 11.69 | N: 11.67 |
| 18.2 | C: 64.76 | C: 64.77 |
|  | H: 8.02 | H: 8.05 |
|  | N: 10.79 | N: 10.80 |
| 18.3 | C: 69.64 | C: 69.68 |
|  | H: 6.64 | H: 6.65 |
|  | N: 11.07 | N: 11.05 |
| 18.4 | C: 69.64 | C: 69.63 |
|  | H: 6.64 | H: 6.63 |
|  | N: 11.07 | N: 11.07 |

TABLE 30-continued

Elemental analysis of the synthesized compounds

| COMPOUND Nr | THEORETICAL % | FOUND % |
|---|---|---|
| 18.5 | C: 59.09<br>H: 6.61<br>N: 11.49 | C: 59.07<br>H: 6.63<br>N: 11.50 |
| 18.6 | C: 57.14<br>H: 6.06<br>N: 10.52 | C: 57.12<br>H: 6.08<br>N: 10.54 |
| 18.7 | C: 60.98<br>H: 7.16<br>N: 10.67 | C: 61.00<br>H: 7.17<br>N: 10.66 |
| 19.1 | C: 72.82<br>H: 7.40<br>N: 4.47 | C: 72.84<br>H: 7.39<br>N: 4.47 |
| 19.2 | C: 73.87<br>H: 7.97<br>N: 4.10 | C: 73.85<br>H: 7.99<br>N: 4.09 |
| 19.3 | C: 72.82<br>H: 7.40<br>N: 4.47 | C: 72.81<br>H: 7.41<br>N: 4.46 |
| 19.4 | C: 68.03<br>H: 6.34<br>N: 4.41 | C: 68.05<br>H: 6.34<br>N: 4.40 |
| 19.5 | C: 76.30<br>H: 7.47<br>N: 4.94 | C: 76.32<br>H: 7.47<br>N: 4.94 |
| 19.6 | C: 73.59<br>H: 8.03<br>N: 8.58 | C: 73.58<br>H: 8.04<br>N: 8.59 |
| 19.7 | C: 73.05<br>H: 7.74<br>N: 8.97 | C: 73.07<br>H: 7.73<br>N: 8.94 |
| 19.8 | C: 72.46<br>H: 7.43<br>N: 9.39 | C: 72.45<br>H: 7.44<br>N: 9.40 |
| 19.9 | C: 67.10<br>H: 6.97<br>N: 3.73 | C: 67.09<br>H: 6.98.<br>N: 3.73 |
| 19.10 | C: 73.37<br>H: 7.70<br>N: 4.28 | C: 73.37<br>H: 7.68<br>N: 4.29 |
| 19.11 | C: 72.61<br>H: 7.42<br>N: 7.36 | C: 72.60<br>H: 7.43<br>N: 7.35 |
| 19.12 | C: 66.56<br>H: 6.98<br>N: 7.76 | C: 66.58<br>H: 6.99<br>N: 7.74 |
| 19.13 | C: 62.59<br>H: 6.71<br>N: 12.17 | C: 62.57<br>H: 6.73<br>N: 12.19 |
| 19.14 | C: 69.54<br>H: 8.27<br>N: 6.76 | C: 69.55<br>H: 8.29<br>N: 6.78 |
| 19.15 | C: 71.46<br>H: 8.99<br>N: 5.95 | C: 71.49<br>H: 9.01<br>N: 5.93 |
| 19.16 | C: 72.25<br>H: 9.30<br>N: 5.62 | C: 72.27<br>H: 9.33<br>N: 5.61 |
| 19.17 | C: 62.98<br>H: 5.82<br>N: 3.67 | C: 62.97<br>H: 5.82<br>N: 3.67 |
| 19.18 | C: 56.72<br>H: 5.86<br>N: 5.09 | C: 56.72<br>H: 5.88<br>N: 5.08 |
| 19.19 | C: 68.37<br>H: 7.82<br>N: 7.25 | C: 68.38<br>H: 7.83<br>N: 7.23 |
| 19.20 | C: 71.46<br>H: 8.99<br>N: 5.95 | C: 71.45<br>H: 9.00<br>N: 5.93 |
| 19.21 | C: 70.87<br>H: 9.15<br>N: 12.72 | C: 70.84<br>H: 9.11<br>N: 12.76 |
| 19.22 | C: 68.72<br>H: 8.39<br>N: 14.57 | C: 68.70<br>H: 8.40<br>N: 14.55 |
| 19.23 | C: 69.87<br>H: 8.80<br>N: 13.58 | C: 69.90<br>H: 8.80<br>N: 13.58 |
| 19.24 | C: 67.39<br>H: 7.92<br>N: 15.72 | C: 67.40<br>H: 7.91<br>N: 15.75 |
| 19.25 | C: 58.28<br>H: 6.67<br>N: 12.36 | C: 58.25<br>H: 6.68<br>N: 12.34 |
| 19.26 | C: 56.47<br>H: 6.16<br>N: 13.17 | C: 56.49<br>H: 6.19<br>N: 13.14 |
| 19.27 | C: 69.87<br>H: 8.80<br>N: 13.58 | C: 69.91<br>H: 8.79<br>N: 13.57 |
| 20.1 | C: 73.45<br>H: 6.16<br>N: 9.52 | C: 73.44<br>H: 6.15<br>N: 9.53 |
| 20.2 | C: 67.78<br>H: 6.26<br>N: 7.90 | C: 67.77<br>H: 6.25<br>N: 7.88 |
| 20.3 | C: 74.51<br>H: 6.88<br>N: 8.69 | C: 74.52<br>H: 6.88<br>N: 8.68 |
| 20.4 | C: 75.40<br>H: 7.48<br>N: 7.99 | C: 75.40<br>H: 7.50<br>N: 7.99 |
| 20.5 | C: 63.01<br>H: 5.77<br>N: 6.68 | C: 63.04<br>H: 5.78<br>N: 6.66 |
| 20.6 | C: 71.98<br>H: 6.04<br>N: 13.99 | C: 72.00<br>H: 6.05<br>N: 13.97 |
| 20.7 | C: 76.16<br>H: 7.99<br>N: 7.40 | C: 76.13<br>H: 8.00<br>N: 7.41 |
| 20.8 | C: 59.26<br>H: 4.97<br>N: 5.76 | C: 59.24<br>H: 4.95<br>N: 5.76 |
| 21.1 | C: 75.87<br>H: 5.97<br>N: 5.53 | C: 75.88<br>H: 5.98<br>N: 5.52 |
| 21.2 | C: 76.84<br>H: 6.81<br>N: 4.98 | C: 76.87<br>H: 6.81<br>N: 4.98 |
| 21.3 | C: 76.38<br>H: 6.41<br>N: 5.24 | C: 76.40<br>H: 6.40<br>N: 5.23 |
| 21.4 | C: 71.45<br>H: 6.64<br>N: 4.90 | C: 71.49<br>H: 6.65<br>N: 4.91 |
| 21.5 | C: 81.24<br>H: 6.82<br>N: 5.57 | C: 81.25<br>H: 6.82<br>N: 5.58 |
| 21.6 | C: 77.26<br>H: 7.17<br>N: 4.74 | C: 77.27<br>H: 7.16<br>N: 4.74 |
| 21.7 | C: 63.55<br>H: 4.39<br>N: 4.36 | C: 63.53<br>H: 4.40<br>N: 4.35 |
| 21.8 | C: 80.69<br>H: 5.87<br>N: 6.27 | C: 80.69<br>H: 5.88<br>N: 6.28 |
| 21.9 | C: 65.16<br>H: 6.11<br>N: 13.41 | C: 65.12<br>H: 6.12<br>N: 13.43 |
| 21.10 | C: 71.13<br>H: 5.97<br>N: 16.59 | C: 71.14<br>H: 5.98<br>N: 16.61 |
| 21.11 | C: 65.09<br>H: 5.46<br>N: 10.84 | C: 65.10<br>H: 5.48<br>N: 10.84 |
| 21.12 | C: 67.10<br>H: 6.34<br>N: 9.78 | C: 67.08<br>H: 6.33<br>N: 9.77 |

TABLE 30-continued

Elemental analysis of the synthesized compounds

| COMPOUND Nr | THEORETICAL % | FOUND % |
|---|---|---|
| 21.13 | C: 81.68<br>H: 7.58<br>N: 5.01 | C: 81.68<br>H: 7.60<br>N: 5.01 |
| 22.1 | C: 76.48<br>H: 5.21<br>N: 5.57 | C: 76.48<br>H: 5.21<br>N: 5.55 |
| 22.2 | C: 72.58<br>H: 5.37<br>N: 4.98 | C: 72.59<br>H: 5.36<br>N: 4.99 |
| 22.3 | C: 77.40<br>H: 6.13<br>N: 5.01 | C: 77.38<br>H: 6.13<br>N: 5.00 |
| 22.4 | C: 68.94<br>H: 7.33<br>N: 5.36 | C: 68.95<br>H: 7.34<br>N: 5.35 |
| 22.5 | C: 77.40<br>H: 6.13<br>N: 5.01 | C: 77.40<br>H: 6.12<br>N: 5.00 |
| 22.6 | C: 68.90<br>H: 5.14<br>N: 4.46 | C: 68.90<br>H: 5.16<br>N: 4.46 |
| 22.7 | C: 77.79<br>H: 6.53<br>N: 4.77 | C: 77.77<br>H: 6.54<br>N: 4.78 |
| 22.8 | C: 74.98<br>H: 5.30<br>N: 9.20 | C: 75.00<br>H: 5.31<br>N: 9.20 |
| 22.9 | C: 70.56<br>H: 8.01<br>N: 4.84 | C: 70.54<br>H: 8.02<br>N: 4.83 |
| 22.10 | C: 71.89<br>H: 8.57<br>N: 4.41 | C: 71.87<br>H: 8.56<br>N: 4.40 |
| 22.11 | C: 73.20<br>H: 5.80<br>N: 4.74 | C: 73.18<br>H: 5.82<br>N: 4.74 |
| 22.12 | C: 75.19<br>H: 7.17<br>N: 3.99 | C: 75.20<br>H: 7.19<br>N: 4.00 |
| 23.1 | C: 66.87<br>H: 5.96<br>N: 4.87 | C: 66.88<br>H: 5.96<br>N: 4.88 |
| 23.2 | C: 67.83<br>H: 6.05<br>N: 14.83 | C: 67.85<br>H: 6.05<br>N: 14.80 |
| 23.3 | C: 71.13<br>H: 5.97<br>N: 16.59 | C: 71.14<br>H: 5.98<br>N: 16.61 |
| 23.4 | C: 65.09<br>H: 5.46<br>N: 10.84 | C: 65.10<br>H: 5.48<br>N: 10.84 |
| 23.5 | C: 63.75<br>H: 4.72<br>N: 8.75 | C: 63.76<br>H: 4.73<br>N: 8.76 |
| 23.6 | C: 65.16<br>H: 6.11<br>N: 13.41 | C: 65.12<br>H: 6.12<br>N: 13.43 |
| 23.7 | C: 74.75<br>H: 5.96<br>N: 4.36 | C: 74.74<br>H: 5.95<br>N: 4.36 |
| 24.1 | C: 67.20<br>H: 6.94<br>N: 12.06 | C: 67.24<br>H: 6.93<br>N: 12.09 |
| 24.2 | C: 68.25<br>H: 7.36<br>N: 11.37 | C: 68.26<br>H: 7.35<br>N: 11.38 |
| 24.3 | C: 58.53<br>H: 5.67<br>N: 10.50 | C: 58.54<br>H: 5.66<br>N: 10.48 |
| 24.4 | C: 64.67<br>H: 5.92<br>N: 13.71 | C: 64.68<br>H: 5.93<br>N: 13.70 |
| 24.5 | C: 55.34<br>H: 4.64<br>N: 11.73 | C: 55.32<br>H: 4.64<br>N: 11.72 |
| 24.6 | C: 70.34<br>H: 6.21<br>N: 8.63 | C: 70.36<br>H: 6.20<br>N: 8.63 |
| 24.7 | C: 74.96<br>H: 7.19<br>N: 8.32 | C: 74.96<br>H: 7.20<br>N: 8.32 |
| 24.8 | C: 69.19<br>H: 7.74<br>N: 10.76 | C: 69.21<br>H: 7.75<br>N: 10.78 |
| 24.9 | C: 64.72<br>H: 6.88<br>N: 10.06 | C: 64.71<br>H: 6.88<br>N: 10.08 |
| 25.1 | C: 64.01<br>H: 7.71<br>N: 9.74 | C: 64.04<br>H: 7.70<br>N: 9.73 |
| 25.2 | C: 63.28<br>H: 7.48<br>N: 10.06 | C: 63.27<br>H: 7.48<br>N: 10.05 |
| 25.3 | C: 66.49<br>H: 6.47<br>N: 9.30 | C: 66.49<br>H: 6.48<br>N: 9.30 |
| 25.4 | C: 65.23<br>H: 5.95<br>N: 9.92 | C: 65.25<br>H: 5.94<br>N: 9.91 |
| 25.5 | C: 56.66<br>H: 6.18<br>N: 9.91 | C: 56.68<br>H: 6.18<br>N: 9.90 |
| 25.6 | C: 54.96<br>H: 6.53<br>N: 8.01 | C: 55.00<br>H: 6.54<br>N: 8.03 |
| 25.7 | C: 58.46<br>H: 6.69<br>N: 9.30 | C: 58.47<br>H: 6.70<br>N: 9.31 |
| 25.8 | C: 61.78<br>H: 5.81<br>N: 8.65 | C: 61.78<br>H: 5.82<br>N: 8.66 |
| 26.1 | C: 56.21<br>H: 5.66<br>N: 6.56 | C: 56.20<br>H: 5.70<br>N: 6.51 |
| 26.2 | C: 67.02<br>H: 7.31<br>N: 7.82 | C: 67.10<br>H: 7.35<br>N: 7.79 |
| 26.3 | C: 58.03<br>H: 6.20<br>N: 6.15 | C: 58.09<br>H: 6.15<br>N: 6.12 |
| 26.4 | C: 68.37<br>H: 7.82<br>N: 7.25 | C: 68.41<br>H: 7.84<br>N: 7.25 |
| 26.5 | C: 51.35<br>H: 5.88<br>N: 5.44 | C: 51.38<br>H: 5.92<br>N: 5.40 |
| 26.6 | C: 63.38<br>H: 7.22<br>N: 5.28 | C: 63.35<br>H: 7.19<br>N: 5.30 |
| 26.7 | C: 60.75<br>H: 6.37<br>N: 5.90 | C: 60.79<br>H: 6.38<br>N: 5.85 |
| 26.8 | C: 70.56<br>H: 8.65<br>N: 6.33 | C: 70.58<br>H: 8.61<br>N: 6.31 |
| 26.9 | C: 65.54<br>H: 8.27<br>N: 6.76 | C: 65.58<br>H: 8.20<br>N: 6.75 |
| 26.10 | C: 71.56<br>H: 6.71<br>N: 4.91 | C: 71.52<br>H: 6.71<br>N: 4.92 |
| 26.11 | C: 75.27<br>H: 6.71<br>N: 5.49 | C: 75.32<br>H: 6.68<br>N: 5.52 |
| 27.1 | C: 72.22<br>H: 7.07<br>N: 4.68 | C: 72.17<br>H: 7.10<br>N: 4.67 |
| 27.2 | C: 70.35<br>H: 6.21<br>N: 8.64 | C: 70.40<br>H: 6.23<br>N: 8.67 |

TABLE 30-continued

Elemental analysis of the synthesized compounds

| COMPOUND Nr | THEORETICAL % | FOUND % |
|---|---|---|
| 27.3 | C: 67.02 | C: 67.10 |
|  | H: 7.31 | H: 7.30 |
|  | N: 7.82 | N: 7.86 |
| 27.4 | C: 58.03 | C: 58.09 |
|  | H: 6.20 | H: 6.18 |
|  | N: 6.15 | N: 6.12 |
| 27.5 | C: 64.77 | C: 64.79 |
|  | H: 6.04 | H: 6.08 |
|  | N: 4.20 | N: 4.25 |
| 27.6 | C: 68.37 | C: 68.33 |
|  | H: 7.82 | H: 7.79 |
|  | N: 7.25 | N: 7.27 |
| 28.1 | C: 63.92 | C: 64.01 |
|  | H: 6.63 | H: 6.65 |
|  | N: 4.38 | N: 4.30 |
| 28.2 | C: 49.11 | C: 49.16 |
|  | H: 5.30 | H: 5.34 |
|  | N: 8.18 | N: 8.20 |
| 28.3 | C: 67.31 | C: 67.27 |
|  | H: 6.98 | H: 7.00 |
|  | N: 4.62 | N: 4.63 |
| 28.4 | C: 64.12 | C: 64.15 |
|  | H: 6.96 | H: 7.01 |
|  | N: 8.80 | N: 8.81 |
| 28.5 | C: 77.11 | C: 77.10 |
|  | H: 7.19 | H: 7.19 |
|  | N: 9.99 | N: 10.13 |
| 28.6 | C: 75.82 | C: 75.86 |
|  | H: 8.10 | H: 8.02 |
|  | N: 16.08 | N: 16.16 |
| 29.1 | C: 58.32 | C: 58.15 |
|  | H: 7.34 | H: 7.40 |
|  | N: 10.20 | N: 10.35 |
| 29.2 | C: 59.22 | C: 60.02 |
|  | H: 7.57 | H: 7.50 |
|  | N: 15.02 | N: 14.99 |
| 29.3 | C: 63.64 | C: 63.70 |
|  | H: 8.28 | H: 8.23 |
|  | N: 11.13 | N: 11.20 |
| 29.4 | C: 60.06 | C: 59.98 |
|  | H: 7.79 | H: 7.83 |
|  | N: 9.55 | N: 9.60 |
| 29.5 | C: 58.20 | C: 58.15 |
|  | H: 6.61 | H: 6.60 |
|  | N: 15.97 | N: 15.92 |
| 29.6 | C: 59.35 | C: 59.39 |
|  | H: 7.83 | H: 7.79 |
|  | N: 13.18 | N: 13.15 |

We claim:

1. A method of preventing or inhibiting the growth of fungi on plants, comprising applying to the plants a fungicidally effective amount of a compound represented by formula (IX):

wherein

Ar is selected from the group consisting of a phenyl group, a naphthyl group, a penta- or hexatomic aromatic heterocyclic group containing from 1 to 4 heteroatoms selected from nitrogen, sulphur and oxygen, said aromatic heterocyclic group possibly being benzo-condensed, a $C_3$–$C_{10}$ cycloalkyl group, a substituted phenyl group, a substituted naphthyl group, a substituted penta- or hexatomic aromatic heterocyclic group containing from 1 to 4 heteroatoms selected from nitrogen, sulphur and oxygen, said aromatic heterocyclic group possibly being benzo-condensed, and a substituted $C_3$–$C_{10}$ cycloalkyl group;

Q is selected from the group consisting of a cyano group, a thiazolic group, a substituted thiazolic group, a group having the general formula (III):

wherein

Y is selected from the group consisting of an oxygen atom, a group having the general formula (IV):

and an AA aminoacidic residue;

$R_b$ is selected from the group consisting of a hydrogen atom, a linear or branched $C_1$–$C_8$ alkyl group, a linear or branched $C_1$–$C_8$ haloalkyl group, a $C_4$–$C_{10}$ cycloalkylalkylic group, a phenyl group, a naphthyl group, a tetra-, penta- or hexatomic heterocyclic group containing from 1 to 4 heteroatoms selected from nitrogen, sulphur and oxygen, said aromatic heterocyclic group being optionally benzo-condensed, a $C_3$–$C_{10}$ cycloalkyl group, a substituted, linear or branched $C_1$–$C_8$ alkyl group, a substituted, linear or branched $C_1$–$C_8$ haloalkyl group, a substituted $C_4$–$C_{10}$ cycloalkylalkylic group, a substituted phenyl group, a substituted naphthyl group, a substituted, tetra-, penta- or hexatomic heterocyclic group containing from 1 to 4 heteroatoms selected from nitrogen, sulphur and oxygen, said aromatic heterocyclic group being possibly benzo-condensed, and a substituted $C_3$–$C_{10}$ cycloalkyl group;

$K_2$ is selected from the group consisting of a direct bond, a linear or branched $C_1$–$C_8$ alkylenic group, a linear or branched $C_1$–$C_8$ haloalkylenic group, a substituted, linear or branched $C_1$–$C_8$ alkylenic group, a substituted, linear or branched $C_1$–$C_8$ haloalkylenic group, and a linear or branched $C_2$–$C_8$ ω-oxa-alkylenic group;

$R_1$ may represent a hydrogen atom, a fluorine atom, a linear or branched $C_1$–$C_8$ alkyl group, a linear or branched $C_1$–$C_8$ haloalkyl group, a substituted, linear or branched $C_1$–$C_8$ alkyl group, or a substituted, linear or branched $C_1$–$C_8$ haloalkyl group;

$R_2$ may represent a hydrogen atom, a fluorine atom, a linear or branched $C_1$–$C_8$ alkyl group, a linear or branched $C_1$–$C_8$ haloalkyl group, a substituted, linear or branched $C_1$–$C_8$ alkyl group, a substituted, linear or branched $C_1$–$C_8$ haloalkyl group, a $C_1$–$C_2$ alkylenic chain which is joined to a carbon atom forming the above Ar group, or a substituted $C_1$–$C_2$ alkylenic chain which is joined to a carbon atom forming the above Ar group;

$R_2$ together with $R_b$ may represent a direct bond when $K_2$ does not represent a direct bond;

$R_2$ together with $R_3$ may represent a linear or branched $C_1$–$C_8$ alkylenic chain, a substituted, linear or branched $C_1$–$C_8$ alkylenic chain, a linear or branched $C_1$–$C_8$ haloalkylenic chain, or a substituted, linear or branched $C_1$–$C_8$ haloalkylenic chain;

$R_2$ together with $R_1$ may represent a linear or branched $C_1$–$C_8$ alkylenic chain, a substituted, linear or branched $C_1-C_8$ alkylenic chain, a linear or branched $C_1-C_8$ haloalkylenic chain, or a substituted, linear or branched $C_1-C_8$ haloalkylenic chain;

$R_3$ may represent a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl or a group having general formula (III) described above;

$R_4$ may represent a hydrogen atom, a linear or branched $C_1-C_8$ alkyl group, a linear or branched $C_1-C_8$ haloalkyl group, a substituted, linear or branched $C_1-C_8$ alkyl group, or a substituted, linear or branched $C_1-C_8$ haloalkyl group;

$R_4$ together with $R_b$ may represent a $C_1-C_2$ alkylenic chain when $K_2$ does not represent a direct bond;

AA represents an aminoacidic residue having general formula (VI):

(VI)

wherein:

L represents a group having general formula (VII):

(VII)

G represents a direct bond, or a group having general formula (VIII):

(VIII)

$R_6$ is selected from the group consisting of a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, and a substituted phenyl group;

$R_7$ is selected from the group consisting of a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, and a substituted phenyl group;

$R_6$ and $R_7$ may also represent, jointly, a linear or branched $C_1-C_8$ alkylenic chain, a linear or branched $C_1-C_8$ thia-alkylenic chain, a linear or branched $C_1-C_8$ oxa-alkylenic chain, a linear or branched $C_1-C_8$ haloalkylenic chain, a substituted, linear or branched $C_1-C_8$ alkylenic chain, a substituted, linear or branched $C_1-C_8$ thia-alkylenic chain, a substituted, linear or branched $C_1-C_8$ oxa-alkylenic chain, or a substituted, linear or branched $C_1-C_8$ haloalkylenic chain;

$R_8$ is selected from the group consisting of a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, and a substituted phenyl group;

$R_9$ is selected from the group consisting of a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, and a substituted phenyl group;

$R_9$, when $R_2$ does not represent a $C_1-C_2$ alkylenic chain, may also represent a $C_1-C_2$ alkylenic chain which is joined to a carbon atom forming the Ar group described above;

$R_9$ together with $R_2$, may represent a linear or branched $C_1-C_8$ alkylenic chain, or a linear or branched $C_1-C_8$ haloalkylenic chain;

$R_{10}$ is selected from the group consisting of a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, and a substituted phenyl group;

$R_{11}$ is selected from the group consisting of a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, and a substituted phenyl group;

$R_7$ and $R_{11}$ may also represent, jointly, a linear or branched $C_1-C_8$ alkylenic chain, a linear or branched $C_1-C_8$ thia-alkylenic chain, a linear or branched $C_1-C_8$ oxa-alkylenic chain, a linear or branched $C_1-C_8$ haloalkylenic chain, a substituted, linear or branched $C_1-C_8$ haloalkylenic chain, a substituted, linear or branched $C_1-C_8$ alkylenic chain, a substituted, linear or branched $C_1-C_8$ thia-alkylenic chain, a substituted, linear or branched $C_1-C_8$ oxa-alkylenic chain, or a substituted, linear or branched $C_1-C_8$ haloalkylenic chain;

$R_c$ may represent a hydrogen atom, a linear or branched $C_1-C_8$ alkyl group, a linear or branched $C_1-C_8$ haloalkyl group, a substituted, linear or branched $C_1-C_8$ alkyl group, a substituted, linear or branched $C_1-C_8$ haloalkyl group, a $C_3-C_{10}$ cycloalkyl group, a substituted $C_3-C_{10}$ cycloalkyl group, a $C_4-C_{10}$ cycloalkylalkylic group, a substituted $C_4-C_{10}$ cycloalkylalkylic group, a phenyl group, a substituted phenyl group, or a group having general formula (III) described above;

$R_c$ together with $R_2$ may represent a linear or branched $C_1-C_8$ alkylenic group, a linear or branched $C_1-C_8$ haloalkylenic group, a substituted, linear or branched $C_1-C_8$ alkylenic group, a substituted, linear or branched $C_1-C_8$ haloalkylenic group;

$R_c$, when $R_2$ is not a $C_1$–$C_2$ alkylenic chain, may also represent a $C_1$–$C_2$ alkylenic chain which is linked to a carbon atom forming the Ar group described above;

$R_c$, when $R_2$ does not represent a $C_1$–$C_2$ alkylenic chain, may also represent a $C_1$–$C_2$ alkylenic chain which is joined to a carbon atom forming the Ar group described above;

$R_c$ together with $R_2$, may represent a linear or branched $C_1$–$C_8$ alkylenic chain, or a linear or branched $C_1$–$C_8$ haloalkylenic chain.

2. The method of claim 1, wherein Ar is a phenyl group.

3. The method of claim 1, wherein Ar is a substituted phenyl group.

4. The method of claim 1, wherein Q is selected from the group consisting of cyano group, a thiazolic group and a substituted thiazolic group.

5. The method of claim 1, wherein Q is a group having the general formula (III).

6. The method of claim 1, wherein Q is —COOH.

7. The method of claim 1, wherein $R_1$ and $R_2$ are each a hydrogen atom.

8. The method of claim 1, wherein $R_1$ and $R_2$ are each other than a hydrogen atom as defined above.

9. The method of claim 1, wherein $R_1$ is a linear or branched $C_1$–$C_8$ alkyl group.

10. The method of claim 1, wherein $R_2$ is a linear branched $C_1$–$C_8$ alkyl group.

11. The method of claim 1, wherein $R_1$ is a linear or branched $C_1$–$C_8$ alkyl group and $R_2$ is a linear or branched $C_1$–$C_8$ alkyl group.

12. The method of claim 1, wherein $R_3$ is a hydrogen atom or a linear or branched $C_1$–$C_8$ alkyl group.

13. The method of claim 1, wherein $R_c$ is a phenyl group or a substituted phenyl group.

14. The method of claim 13, wherein $R_c$ is a phenyl group.

15. The method of claim 13, wherein $R_c$ is a substituted phenyl group.

16. The method of claim 1, wherein

Ar is a phenyl group or a substituted phenyl group;
Q is a group having the general formula (III);
$R_1$ is a hydrogen atom or a linear or branched $C_1$–$C_8$ alkyl group;
$R_2$ is a hydrogen atom or a linear or branched $C_1$–$C_8$ alkyl group;
$R_3$ is a hydrogen atom or a $C_1$–$C_8$ alkyl group; and
$R_c$ is a phenyl group or a substituted phenyl group.

17. The method of claim 16, wherein $R_1$ and $R_2$ are each a hydrogen atom.

18. The method of claim 16, wherein $R_1$ is a linear or branched $C_1$–$C_8$ alkyl group and $R_2$ is a linear or branched $C_1$–$C_8$ alkyl group.

* * * * *